(12) United States Patent
Doherty

(10) Patent No.: US 10,734,106 B2
(45) Date of Patent: Aug. 4, 2020

(54) SYSTEM AND METHOD FOR FILLING A PRESCRIPTION

(71) Applicant: Tiny Maple Ventures Inc., Toronto (CA)

(72) Inventor: Ryan Doherty, Toronto (CA)

(73) Assignee: Tiny Maple Ventures Inc., Toronto (CA)

( * ) Notice: Subject to any disclaimer, the term of this patent is extended or adjusted under 35 U.S.C. 154(b) by 0 days.

(21) Appl. No.: 15/753,836

(22) PCT Filed: Aug. 18, 2016

(86) PCT No.: PCT/CA2016/050969
§ 371 (c)(1),
(2) Date: Feb. 20, 2018

(87) PCT Pub. No.: WO2017/027974
PCT Pub. Date: Feb. 23, 2017

(65) Prior Publication Data
US 2018/0240539 A1 Aug. 23, 2018

Related U.S. Application Data

(60) Provisional application No. 62/207,416, filed on Aug. 20, 2015.

(51) Int. Cl.
*G16H 20/10* (2018.01)
*G06Q 50/22* (2018.01)
(Continued)

(52) U.S. Cl.
CPC ............. *G16H 20/10* (2018.01); *G06Q 50/22* (2013.01); *G16H 10/60* (2018.01); *G16H 70/40* (2018.01)

(58) Field of Classification Search
CPC ........ G16H 20/10; G16H 10/60; G16H 10/40; G06Q 50/22
(Continued)

(56) References Cited

U.S. PATENT DOCUMENTS 8,175,891 B2 * 5/2012 Berkelhamer ...... G06F 19/3456
705/2
8,326,455 B2 * 12/2012 Dunn .................. G06F 19/3462
700/237
(Continued)

FOREIGN PATENT DOCUMENTS

WO    WO 2008/089249 A1    7/2008
WO    WO-2008089249 A1 *   7/2008  ......... G06F 19/3456

OTHER PUBLICATIONS

International Preliminary Report on Patentability, for International Appl. No. PCT/CA2016/050969, filed Aug. 18, 2016, 10 pages, dated Feb. 20, 2018.
(Continued)

*Primary Examiner* — Rakesh Kumar
(74) *Attorney, Agent, or Firm* — Sterne, Kessler, Goldstein & Fox P.L.L.C.

(57) ABSTRACT

Described herein are methods and systems for filling a medical prescription. One implementation comprises a central prescription handling engine comprising a server and a database, which is in communication with a computing device of a given user via a wide-area network and configured to receive prescription data corresponding to the medical prescription. The central prescription handling engine selectively routes the received prescription data to a given pharmacy interface among a plurality of pharmacy interfaces and selectively routes scheduling data received at the given pharmacy interface for communication to the given user. The given pharmacy interface is in communication with the central prescription handling engine and is config-
(Continued)

ured to receive the prescription data from the central prescription handling engine and to communicate to the central prescription handling engine the scheduling data corresponding to the prescription data.

23 Claims, 13 Drawing Sheets

(51) Int. Cl.
*G16H 10/60* (2018.01)
*G16H 70/40* (2018.01)

(58) Field of Classification Search
USPC .................. 364/479, 413.02, 413.03, 513.5; 700/242; 221/2, 9, 15, 197
See application file for complete search history.

(56) References Cited

U.S. PATENT DOCUMENTS

| | | | | |
|---|---|---|---|---|
| 8,364,504 B1* | 1/2013 | Bleser | ................... | G06F 19/326 |
| | | | | 705/3 |
| 10,235,499 B1* | 3/2019 | Bleser | ................... | G06F 19/326 |
| 10,311,536 B1* | 6/2019 | Ansari | ................... | G06Q 10/10 |
| 2009/0006126 A1* | 1/2009 | Champigny | ........... | G06Q 50/22 |
| | | | | 705/2 |
| 2012/0253832 A1 | 10/2012 | John et al. | | |
| 2015/0242592 A1* | 8/2015 | Weiss | ................. | G06F 19/3456 |
| | | | | 705/2 |
| 2018/0240539 A1* | 8/2018 | Doherty | ................. | G06Q 50/22 |
| 2018/0285533 A1* | 10/2018 | Farhat | ................. | G06F 19/3418 |
| 2018/0286506 A1* | 10/2018 | Farhat | ................. | G06F 19/3418 |

OTHER PUBLICATIONS

Hardy, I., "PopRx, the 'Uber of prescriptions,' launches in Toronto," printed from https://mobilesyrup.com/2015/11/24/poprx-the-uber-of-prescriptions-launches-in-toronto/, 9 pages, Nov. 24, 2015.

Silverberg, D., "Get ready for the Uberization of pharmacy", printed from http://pharmacyu.ca/2016/05/12/get-ready-for-the-uberization-of-pharmacy/, 4 pages, May 12, 2016.

Homepage and Screen captures from YouTube video clip entitled "Dragon's Den Next Gen Den: PopRx," 17 pages, uploaded on Oct. 7, 2015 by user "Dragon's Den," Retrieved from Internet: < https://www.youtube.com/watch?v=D5_wXIJUxps>.

* cited by examiner

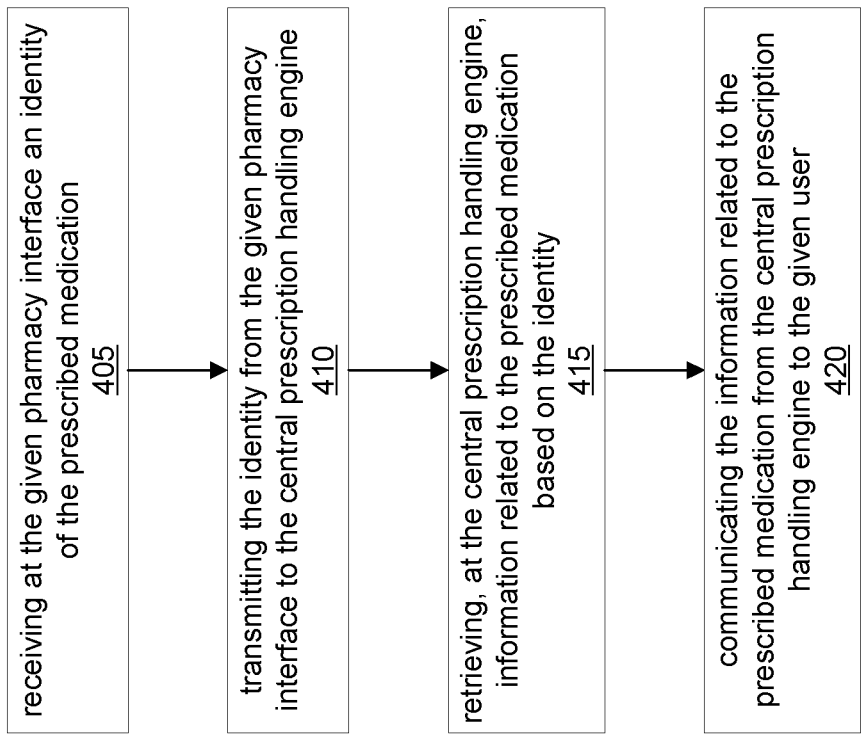
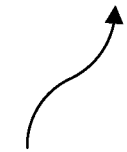
Fig. 4

SYSTEM AND METHOD FOR FILLING A PRESCRIPTION

REFERENCE TO CROSS-RELATED APPLICATIONS

The present application claims priority from U.S. Provisional Application No. 62/207,416 filed on Aug. 20, 2015, the contents being incorporated herein by reference.

FIELD

The specification relates to a system and method for filling a medical prescription.

BACKGROUND

Filling a medical prescription typically requires taking a physical copy of the prescription to the pharmacy, waiting for a period of time for the prescription to be filled, and then physically picking up the prescription. The waiting time can depend on a number of factors including whether the prescribed medication is in stock, the number of other prescriptions that the pharmacy must fill, and the capacity of the pharmacy to fill those prescriptions. In some instances, with known systems, medical prescriptions may be sent digitally with limited patient choice and engagement. In some of these instances, pharmacies will not prepare the medication in advance because the patient may never pick-up the prescription.

While the pharmacy may have information internally regarding its inventory and prescription filling capacity, that information is typically not accessible outside a specific pharmacy location or chain of pharmacies. There are also limited processes for communicating this information to customers in advance to allow them to plan around the wait time. Known techniques for communicating information are not suitable for medical prescriptions because they do not allow the customer to efficiently search for a desirable pharmacy among a plurality of available pharmacies, and to direct the prescription to the pharmacy with desired characteristics such as geographical proximity and suitable operating hours. In other words, known techniques and systems do not allow for a solution that is tailored to the customer's needs and the pharmacy's capabilities, including the pharmacy's IT capability, to fulfill those needs. In addition, known techniques do not allow for easy storage and tracking of communications between the customer and the pharmacy, and as such do not facilitate providing continuing and actively-monitored care to the customer.

SUMMARY

According to some implementations, there is provided a system for filling a medical prescription which comprises a central prescription handling engine. The central prescription handling engine comprises a server and a database, and is in communication with a computing device of a given user via a wide-area network. The central prescription handling engine is configured to receive prescription data corresponding to the medical prescription. The central prescription handling engine is configured to selectively route the prescription data received at the central prescription handling engine to a given pharmacy interface among a plurality of pharmacy interfaces and to selectively route scheduling data received at the given pharmacy interface for being communicated to the given user. The given pharmacy interface is in communication with the central prescription handling engine, and the given pharmacy interface is configured to receive the prescription data from the central prescription handling engine and communicate the scheduling data corresponding to the prescription data to the central prescription handling engine.

According to some implementations, the central prescription handling engine is configured to receive the prescription data from the computing device of the given user.

According to some implementations, the central prescription handling engine is in communication with a computing device of a prescribing entity and the central prescription handling engine is further configured to receive the prescription data from one of a computing device of the given user and the computing device of the prescribing entity.

According to some implementations, the system for filling a medical prescription further comprises an intermediary pharmacy interface. The intermediary pharmacy interface can be associated with a subset of pharmacy interfaces of the plurality of pharmacy interfaces which comprises the given pharmacy interface, and is in communication with the given user interface and the central prescription handling engine via the wide-area network. The intermediary pharmacy interface is configured to receive the prescription data selectively routed from the central prescription handling engine instead of the given pharmacy interface, receive the scheduling data from the given pharmacy interface, and transmit the scheduling data received from the given pharmacy interface to the central prescription handling engine. The given pharmacy interface is in communication with the central prescription handling engine via the intermediary pharmacy interface.

According to another implementation, there is provided a method of filling a medical prescription that comprises receiving at a central prescription handling engine prescription data of the medical prescription listing a prescribed medication. The central prescription handling engine is configured to selectively route the prescription data received at the central prescription handling engine to a given pharmacy interface among a plurality of pharmacy interfaces and to selectively route scheduling data received at the given pharmacy interface for being communicated to the given user. The method further comprises transmitting the prescription data from the central prescription handling engine to the given pharmacy interface, receiving at the given pharmacy interface the scheduling data corresponding to the image, transmitting the scheduling data from the given pharmacy interface to the central prescription handling engine, and communicating the scheduling data from the central prescription handling engine to the given user. According to some implementations, the prescription data comprises at least one of an image of the medical prescription and structured metadata of the medical prescription.

Further aspects of the present invention are described below and in the claims.

BRIEF DESCRIPTION OF THE DRAWINGS

For a better understanding of the various implementations described herein and to show more clearly how they may be carried into effect, reference will now be made, by way of example only, to the accompanying drawings in which:

FIG. 4 depicts another example method of filling a medical prescription, according to a non-limiting implementation;

DETAILED DESCRIPTION

Figure 1:
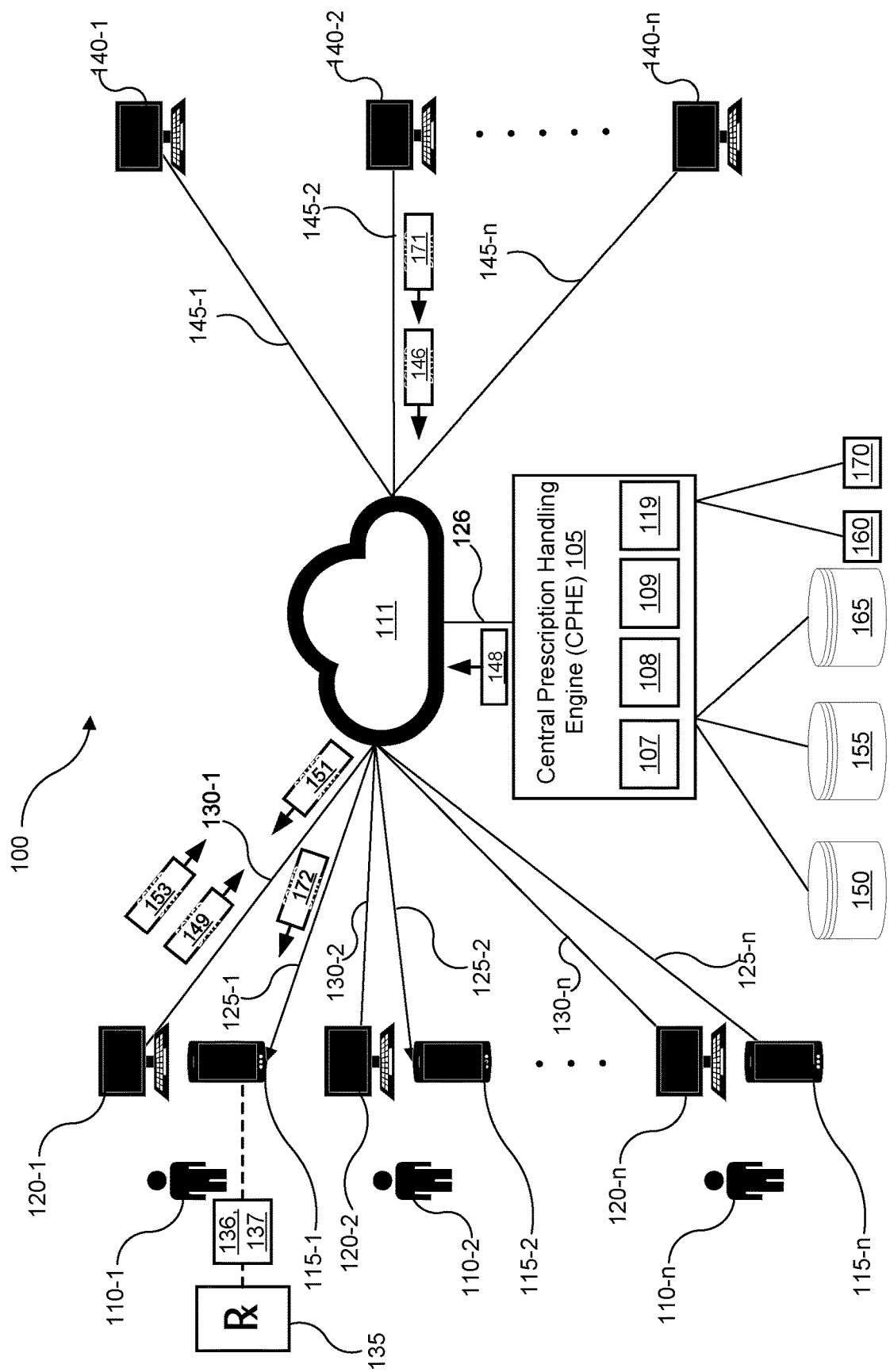
FIG. 1 depicts an example system for filling a medical prescription, according to first non-limiting implementation.

In the present specification, elements may be described as "configured to" perform one or more functions or "configured for" such functions. In general, an element that is configured to perform or configured for performing a function is configured to perform the function, or is suitable for performing the function, or is adapted to perform the function, or is operable to perform the function, or is otherwise capable of performing the function.

It is understood that for the purpose of this specification, language of "at least one of X, Y, and Z" and "one or more of X, Y and Z" can be construed as X only, Y only, Z only, or any combination of two or more items X, Y, and Z (e.g., XYZ, XYY, YZ, ZZ, and the like).

It is also understood that references to "information", "request", "confirmation", and "notification" are, unless otherwise specified, also references to data that is indicative of and/or comprising the described "information", "request", "confirmation", "notification".

The system and methods for filling a medical prescription described herein allow for routing communications between healthcare professionals, such as physicians and nurses to pharmacists affiliated with a prescribing entity (e.g., a medical clinic, hospital and the like), or a customer/user and an interface corresponding to a pharmacy selected among a plurality of available pharmacies. In some implementations, a central prescription handling engine receives prescription data corresponding to a medical prescription from a user (via a computing device of the user). In some implementations, the central prescription handling engine receives the prescription data from a prescribing entity, such as a clinic or hospital that is associated with at least one prescriber (e.g., a doctor, a nurse practitioner, or other individual authorized by a recognized health care licensing entity to prescribe medications) (via a computing device or interface of the prescribing entity). In some implementations the prescription data can be received by the central prescription handling engine from either the user or the prescribing entity. The central prescription handling engine routes that prescription data to the selected pharmacy. Before sending the prescription data to a given pharmacy, the user can be presented with a list of available pharmacies and provided with the ability to choose which pharmacy will receive the user's prescription data. The list of available pharmacies provided to the user can be based on a number of criterion. For example, the list of pharmacies can be based on the physical proximity of candidate pharmacies to the user, the ability of the candidate pharmacies to receive the prescription data and the processing capacity of a computing system of the candidate pharmacy. As such, the central prescription handling engine may reduce the time, bandwidth, and processing power that would be needed if the user had to find and review each available pharmacy individually and potentially communicate with each available pharmacy individually.

In some implementations, the prescription data can be transmitted in the form of a digital image or image data of the prescription. In some implementations, the prescription data can be transmitted in the form of structured metadata that may also comprise the image of the prescription. The prescription data can comprise information in other formats, such as a bar code, QR code, and/or text that can also be communicated and processed. This obviates the need for the user and/or the prescription to be physically present at the selected pharmacy to initiate the prescription filling process. Once the prescription data is communicated to the selected pharmacy, scheduling data related to the filling of the prescription is communicated from the pharmacy to the central prescription handling engine, which in turn routes and communicates the scheduling data to the user. The user can additionally or alternatively comprise a requested scheduling data (e.g., a preferred pick up time) with the prescription information. This allows the user to plan around the wait time while the prescription is being filled.

In some implementations, the pharmacy is affiliated with other pharmacies, for example, by a common owner (such as a company or human individual) or geographic location. In such implementations, it may be more efficient in terms of computing resources to centralize the processing of the prescription data and the scheduling data of each of these affiliated pharmacies. For example, in some implementations, the prescription data is not transmitted directly from the central prescription handling engine to the pharmacy (or a computing device or system associated with the pharmacy). Instead, the prescription data is transmitted to an intermediary pharmacy computing interface that is in communication with the given pharmacy interface. In response to receiving the prescription data from the central prescription handling engine, the intermediary pharmacy computing interface can transmit a notification of the prescription to each of the affiliated pharmacies. In response to receiving the notification, at least one of the affiliated pharmacies transmit scheduling data to the intermediary pharmacy computing interface, which is then transmitted to the central prescription handling engine. The central prescription handling engine routes and communicates the scheduling data to the user. The intermediary pharmacy interface can be associated with a back end pharmacy that prepares the medication and delivers it to the retail pharmacy location selected by the user to pick up the medication from.

In addition, the central prescription handling engine can store and track the communications between the user and the pharmacy to facilitate provision of continuing and actively-monitored care. For example, the central prescription handling engine can inform the user about medication side-effects or interactions, and can remind the user about compliance, e.g., when/how to take the medication, and about prescription refills. Moreover, the central prescription handling engine can provide a central hub for integrating insurance and payment engines with the prescription filling process, which can further reduce the time and effort, particularly in respect of computing resources, required to complete the prescription filling process.

Communications described herein, such as those bearing prescription data, prescription images, payment information, and similar may be encrypted. It is understood that any suitable method and means for encrypting the respective data, information and the like is contemplated.

FIG. 1 shows an example system 100 for filling a medical prescription 135 listing one or more prescribed medications and/or treatments. The system 100 comprises a central prescription handling engine (CPHE) 105, which in turn comprises a server 107 and a data storage 109 (also referred to herein as database 109). The server 107 can comprise one or more processors 108 configured to execute instructions, which may originate from the data storage 109 or a computer network. The processor 108 may be known as a Central Processing Unit (CPU). The processor 108 can comprise one or more sub-processors or processing cores. In some implementations, the data storage unit 109 can comprise a non-transitory machine-readable medium that is configured to store programs and data. In some implementations, the data storage 109 can also comprise one or more short-term or long-term storage devices, such as a solid-state memory chip (e.g., Dynamic Random-Access Memory (DRAM), Read-Only Memory (ROM), non-volatile flash memory), a hard drive, an optical storage disc, and similar. The data storage 109 can comprise one or both of fixed components that are not physically removable (e.g., fixed hard drives) and removable components (e.g., removable memory cards). The data storage 109 allows for random access, in that programs and data may be both read and written.

The processor 108 and data storage 109 operate in conjunction to execute the functionality of CPHE 105 discussed herein. Although one server 107 and one data storage 109 are shown, it is contemplated that multiple of such servers and data storage components can be used to implement the functionality described herein. Various functional components of CPHE 105 need not be co-located. CPHE 105 can also have network interfaces for communication with networks and other devices.

In some implementations, the CPHE 105 is owned and operated by a private entity. In some implementations, the CPHE 105 is owned and operated by a public entity or a quasi-public entity. For example, in some implementations, the CPHE 105 is owned and operated by a governmental agency or body.

CPHE 105 is in communication with at least one computing device of a given user via one or more communication links, which can be a combination of wired and/or wireless communication links. The communication links can form part of a wide-area network, such as network 111. The given user can be one of a plurality of users 110 in communication with the CPHE 105. For example, the user's computing device can be a mobile device, such as the mobile device 115-1 of a user 110-1 and the CPHE 105 is in communication with the mobile device 115-1 via link 125-1 and link 126, and at least with one or more of mobile device 115-2 of user 110-2 via link 125-2 and link 126, and mobile device 115-n of user 110-n via link 125-n and link 126. Mobile devices 115-1 to 115-n can include, but are not limited to, smartphones and wearable electronic devices. CPHE 105 can be in communication with two or more mobile devices of two or more users, respectively. The communication between CPHE 105 and the mobile devices 115-1 to 115-n can be through links 125-1 to 125-n and 126 which can comprise any wired and/or wireless network including, but not limited to, a wide-area network, such as network 111, and a cellular network, and any suitable combination thereof.

User 110-1 can also have a web account or web portal accessible through a web-connected terminal 120-1, which can be in communication with CPHE 105 via link 130-1. Terminal 120-1 can be a Personal Computer or any other device capable of accessing the web account. Link 130-1 can comprise any suitable wired, wireless, or a combination of wired and wireless connections. Web accounts, terminals, and terminal-to-CPHE 105 links can be similar for the other users. For example, user 110-2 can have a web account accessible through terminal 120-2 in communication with CPHE 105 via link 130-2, and user 110-n can have a web account accessible through terminal 120-n in communication with CPHE 105 via link 130-n. In some implementations, the web account of a user can be also accessible through a browser or other application running on the mobile device of that user. Through the web account, patients can view scheduled appointments, wait-times and virtual queuing information. Patients can also record and view personal preferences (insurance coverage, preferred pharmacy locations, preferred pick-up times) and medical information (known allergies, current medications, past medications).

CPHE 105 is also in communication with a plurality of pharmacy interfaces 140-1, 140-2 to 140-n (referred to collectively as plurality of pharmacy interfaces 140), via links 145-1, 145-2 to 145-n respectively, which links can comprise wired, wireless, or a combination of wired and wireless connections. Each pharmacy interface 140-1 to 140-n can represent one or more physical or virtual pharmacies, or combination thereof. Herein "a virtual pharmacy" is considered a pharmacy that does not have a retail location but provides pharmacy services, such as filling prescriptions, online (e.g., over the Internet). For example, a "virtual pharmacy" can have or be associated with a warehouse or physical establishment that fills prescriptions ordered via its respective pharmacy interface. In contrast, a physical pharmacy is described herein as a pharmacy having at least one retail location in which users can physically pick up their filled prescriptions. Pharmacy interface 140-1 to 140-n can be a terminal through which a staff member of the pharmacy sends and receives information to and from the CPHE 105, respectively. Pharmacy interface 140-1 to 140-n can also comprise a connection point between the internal IT systems of the corresponding pharmacy and CPHE 105. Pharmacy interfaces 140-1 to 140-n can also be accessed through a special pharmacy web account that provides additional information about prescription requests, queued prescriptions, delivery/pick-up scheduling, and associated notifications. Notifications could also be sent via email, SMS or other communication methods to inform a pharmacist or staff that they need to respond to an enquiry through the respective pharmacy interface.

For illustrative purposes only, the following description will focus on user 110-1 and his/her mobile device 115-1 and terminal 120-1, and on pharmacy interface 140-2. However, the description is applicable to any one of the plurality of users 110, and his/her computing device, such as his/her mobile device and terminal, and to any one of the plurality of pharmacy interfaces 140. User 110-1 sends prescription data 136 that corresponds to a medical prescription 135. For example, the prescription data 136 can correspond to an image 137 of the medical prescription 135 that is captured by user 110-1 using his/her mobile device 115-1. In some implementations, the prescription data 136 comprises the image 137. The image 137 could be temporarily stored within the mobile application or transmitted from the mobile device to the CPHE 105 as a compressed and encrypted image file. In some implementations, after capturing the image 137, the CPHE 105 requests the user 110-1 to provide user profile information, such as an account number and user identification number. Alternatively, in some implementations, the requested profile information is pre-stored at the CPHE 105 or at the computing device of user 110-1, such as mobile device 115-1. The image 137 can also be stored in the CPHE 105 linking it to information about the user, submission timestamp, and prescription-related information. In some implementations, the prescription data 136 comprises structured data or metadata (e.g., in Extensible Markup Language (XML), Health Level 7 (HL7) formats) that is generated based on the image 137 and the requested user profile information, but does not comprise the image 137. In some implementations, the structured data or metadata comprises the image 137. In other words, in some implementations, the prescription data 136 comprises at least one of the image 137 and structured data or metadata corresponding to the medical prescription. In some implementations, at least a portion of the structured data or metadata is generated by the computing device of the user 110-1, such as mobile device 115-1. The prescription data 136 can be sent via link 125-1 to CPHE 105, which is configured to selectively route the prescription data 136, for example to pharmacy interface 140-2, among the plurality of pharmacy interfaces 140-1 to 140-n. Prescription data 136 can also be captured and/or generated using a device other than mobile device 115-1, for example a digital camera, and uploaded through terminal 120-1 or mobile device 115-1 for communication to CPHE 105. Selective routing could either be based on user choice, or could be automated using preferences stored by user (pharmacy location/chain, day/time for pick-up/delivery, pharmacy operating hours, insurance coverage, language spoken, medication availability, prescription queue length, pharmacy staff availability, etc). The selective routing can be based on selections of user 110-1, or can be performed automatically based on characteristics of each pharmacy corresponding to each pharmacy interface 140-1 to 140-n, as will be discussed further below.

Although FIG. 1 depicts the prescription data 136 being transmitted from a computing device of user 110-1, in some implementations the prescription data 136 is transmitted from a computing device or interface associated with another entity, such as a prescribing entity. An example system in which the prescription data can be transmitted from a computing device or interface associated with an entity other than the user is described further below.

Since pharmacy interface 140-2 is chosen, for illustrative purposes only, as the recipient of the prescription data 136 of medical prescription 135, pharmacy interface 140-2 will henceforth be referred to as "given pharmacy interface (GPI)" 140-2 to distinguish it from the other pharmacy interfaces that do not receive prescription data 136 of medical prescription 135. Similarly, user 110-1 who is, for illustrative purposes only, the source of the communication to GPI 140-2, will henceforth be referred to as "given user 110-1".

GPI 140-2 receives prescription data 136 corresponding to medical prescription 135 from CPHE 105 via link 145-2 (and link 126), and communicates the prescription data 136 to CPHE 105 via link 145-2 (and link 126) scheduling data 146 corresponding to prescription data 136. CPHE 105 is also configured to selectively route scheduling data 146 received at GPI 140-2 for being communicated to the given user 110-1, who initially sent prescription data 136 corresponding to medical prescription 135 to CHPE 105. Selective routing could either be based on user choice, or could be automated using preferences stored by user (e.g., pharmacy location/chain, day/time for pick-up/delivery, pharmacy operating hours, insurance coverage, language spoken, medication availability, prescription queue length, pharmacy staff availability, operational efficiency and capacity of the computing system or systems of the respective pharmacy, etc.). Queue position and/or queue time information and/or specific delivery timestamp and/or specific pick-up timestamp would be communicated to given user 110-1.

In some implementations, instead of sending prescription data 136 of medical prescription 135, CPHE 105 can process prescription data 136 and sends modified prescription data 148, related to or extracted from prescription data 136, to GPI 140-2. In such an implementation, the scheduling data received at GPI 140-2 corresponds to the image data received at GPI 140-2 from CPHE 105. In some implementations, processing prescription data 136 of medical prescription 135 can comprise extracting at least a portion of the textual information or other identifiable information (e.g., a QR code) contained in image 137 or associated with image 137. Such textual information or other identifiable information can comprise the identity of the prescribed medication, dose and frequency of administration, the number and quantity of refills, identity of the patient/user, and identity of the prescribing physician. In some implementations, processing prescription data 136 of medical prescription 135 can comprise extracting unique symbols (e.g., barcode or QR code), structured data or metadata that are associated with the identity of the prescribed medication, dose, frequency of administration, number and quantity of refills, identity of patient, and prescribing physician.

Figure 2:
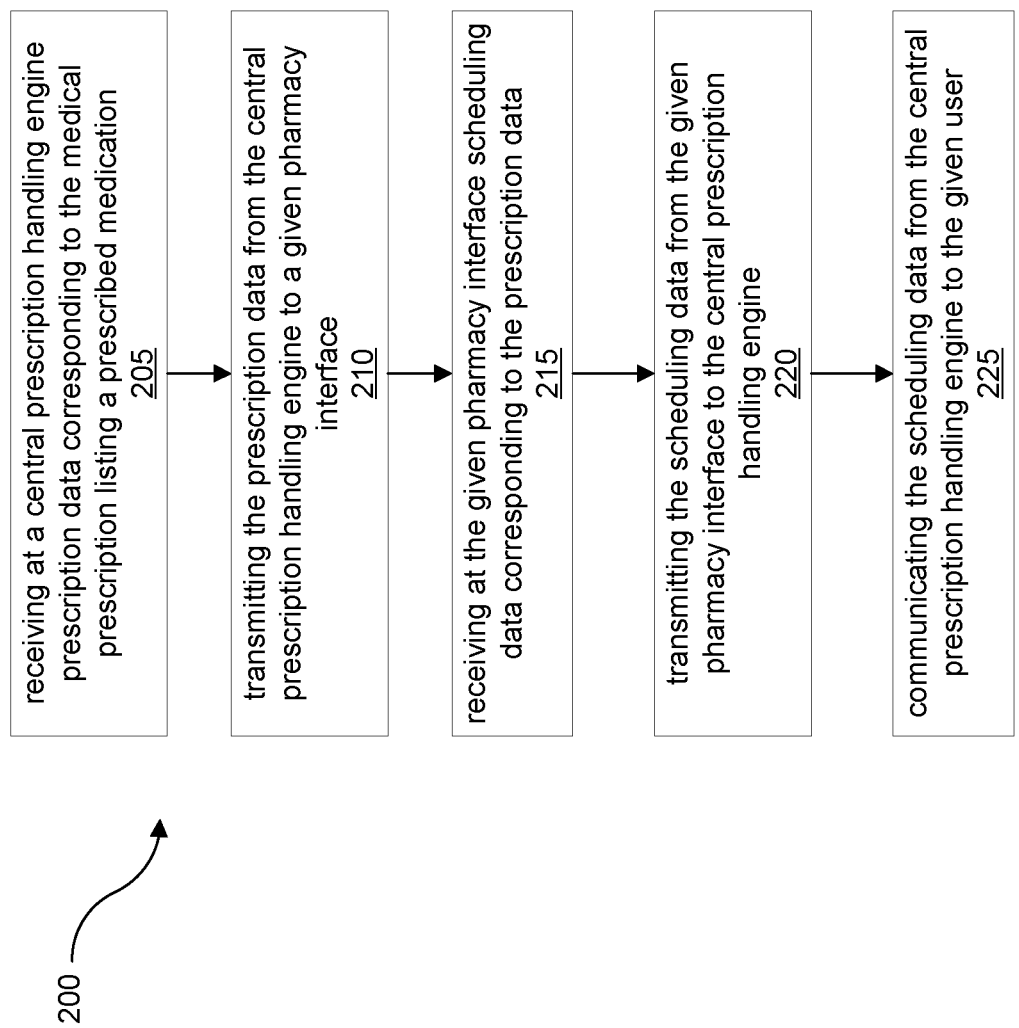
FIG. 2 depicts an example method of filling a medical prescription, according to a non-limiting implementation.

As shown in example method 200 represented in FIG. 2, in operation at step 205 CPHE 105 receives prescription data 136 corresponding to the medical prescription 135 listing one or more prescribed medications. For example, the prescription data 136 can be received from a computing device of the user 110-1, such as mobile device 115-1. However, in some implementations, at step 205, the prescription data can be received from a computing device or interface other than that associated with the user 110-1. As discussed above the prescription data 136 can comprise image 137 of the medical prescription that is captured at mobile device 115-1, or other computing device, of given user 110-1. At step 210, CPHE 105 selectively routes and transmits prescription data 136 to GPI 140-2. The selective routing can be based on selection of given user 110-1, and/or based on default criteria stored at CPHE 105 and applied to select pharmacies, or number of pharmacies, among the pharmacies corresponding to pharmacy interfaces 140-1 to 140-n. At step 215, GPI 140-2 receives scheduling data 146 corresponding to prescription data 136. The scheduling data 146 can comprise at least one of an appointment for given user 110-1 to attend at a pharmacy corresponding to or otherwise associated with GPI 140-2, henceforth referred to as the "given pharmacy", to retrieve the prescribed medication listed on medical prescription 135 and an indication of a start time from which the prescribed medication is available for retrieval from the given pharmacy GPI 140-2. The prescription data 137 can be transmitted from a computing device of the user 110-1, such as the mobile device 115-1, to the CPHE 105 as a compressed and encrypted image file. The image file can be stored in the CPHE 105 linking it to information about the user 110-1, submission timestamp, and prescription-related information. The prescription data 136 will be transmitted from CPHE 105 to GPI 140-2 as a compressed and encrypted image file, and the pharmacy associated with GPI 140-2 can also access associated information within the CPHE 105.

In some implementations, a staff member of the given pharmacy accesses the prescription data 136 at GPI 140-2 and determines the time of the appointment, or the start time for availability of the prescribed medication, based on at least one of the availability of the prescribed medication at the given pharmacy, e.g., whether the prescribed medication is in stock, a prescription filling capacity of the given pharmacy. The prescription filling capacity can be determined based on staffing levels, number of prescriptions that have to be filled, and the complexity of prescriptions being filled. In other implementations, an internal IT system of the pharmacy, for example an automated workflow management system, provides optimal appointment times to GPI 140-2. In some implementations, the automated workflow management system generates optimal appointment times based on staffing, which may increase and/or decrease in response to a change in demand for the given pharmacy's services, or other services.

In some implementations, given user 110-1 can also provide his/her availability data 149 to CPHE 105. Given user 110-1 can enter his/her availability data 149 at a computing device, such as mobile device 115-1, or through his/her web account accessible, for example, through terminal 120-1. Availability data 149 can also be provided automatically through a calendar application on mobile device 115-1, or other computing device of the user 110-1. CPHE 105 can then transmit this availability data 149 over link 145-2 to GPI 140-2. The appointment received at GPI 140-2 can be based on this availability data of given user 110-1.

At step 220, scheduling data 146 is transmitted over link 145-2 from GPI 140-2 to CPHE 105. At step 225, CPHE 105 communicates the scheduling data 146 to given user 110-1. Scheduling data 146 can be communicated to given user 110-1 by transmitting the scheduling data 146 from CPHE 105 over a wide-area network, such as network 111, or a cellular network, or any suitable combination thereof, to a computing device of the user 110-1, such as mobile device 115-1 via communication links 125-1 and 126. It is understood that any suitable manner of transmitting the scheduling data 146 to a computing device of the user, such mobile device 115-1, via the respective communication link or combination of communication links is contemplated. In some implementations, the scheduling data 146 can be presented as a calendar invitation on mobile device 115-1. In other implementations, scheduling data 146 can be automatically recorded as an appointment in the calendar application running on mobile device 115-1. In some implementations, scheduling data 146 can be presented to the user 110-1 as a notification of the start time or start date and time from which the prescribed medication will be available.

In other implementations, communicating the scheduling data to given user 110-1 can comprise making the scheduling data 146 available through the web account accessible by given user 110-1. For example, the web account can be accessible via terminal 120-1 or through mobile device 115-1, or another computing device accessible to the user 110-1. Through the web account, given user 110-1 can view information about future scheduled appointments, pick-ups and deliveries, and historical appointments, pick-ups and deliveries. This information can be displayed as a calendar and list. Notifications and reminders of upcoming appointments, pick-ups and deliveries can also be received through e-mail, SMS, app notification, etc. The web account can be personalized, for example by password protection, to allow only given user 110-1 to access the information, including the scheduling data 146, available through the web account.

In some implementations, the scheduling data 146 can comprise a position of given user 110-1 in a virtual queue at the given pharmacy. The virtual queue can comprise a sequence for serving the customers in the order in which they submit their prescriptions for being filled. That is, in such a queue, the first customer to submit his/her prescription is served first, with the second customer being served next, i.e., second, and so on. "First", "second", etc. would be positions in such a virtual queue.

Figure 3:
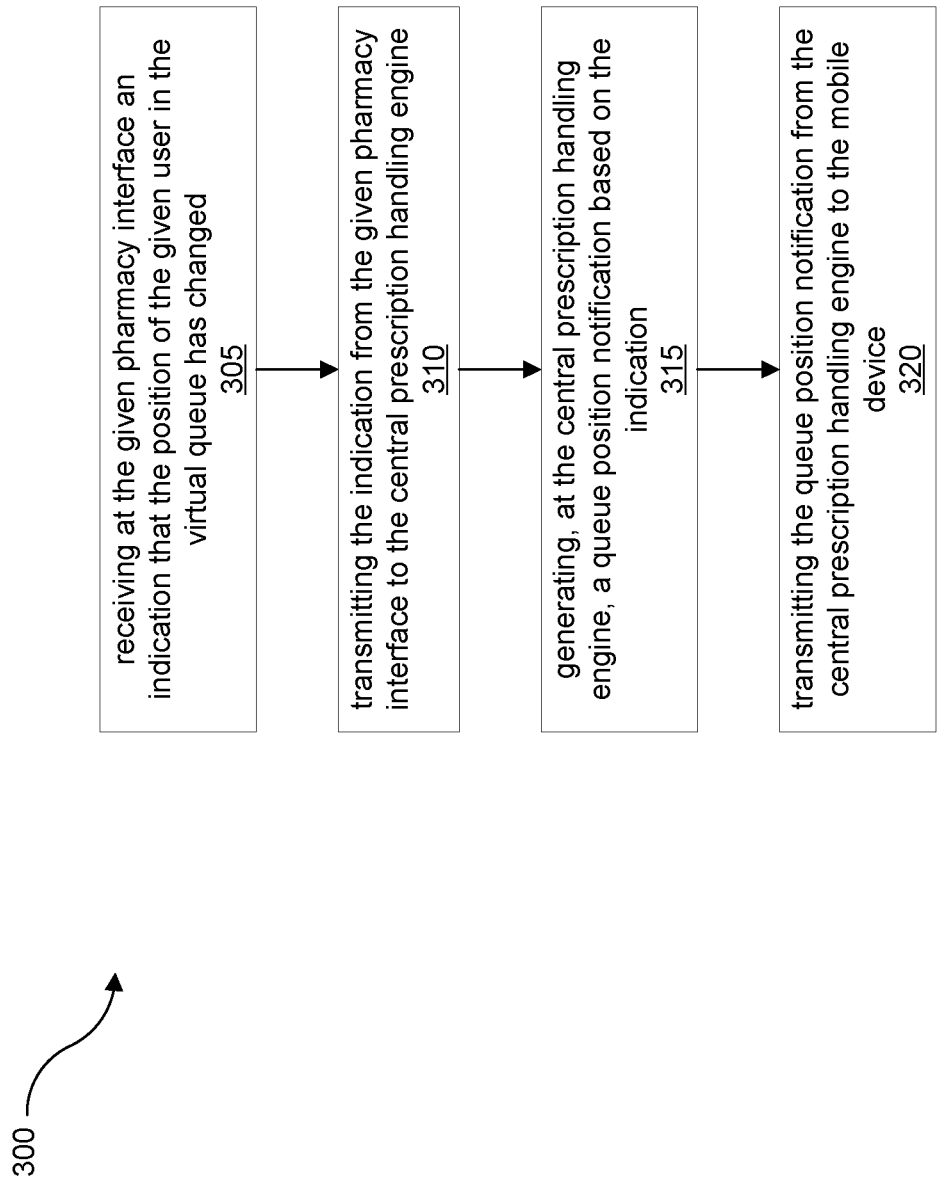
FIG. 3 depicts another example method of filling a medical prescription, according to a non-limiting implementation.

In some implementations, as shown in example method 300 represented in FIG. 3, at step 305, GPI 140-2 can receive an indication that the position of given user 110-1 in the virtual queue has changed. This indication can be manually entered at GPI 140-2 by a staff member of the given pharmacy, or can be communicated to GPI 140-2 by an automated and/or IT system of the given pharmacy. The indication can be a result of a customer ahead of given user 110-1 in the virtual queue being served, and given user 110-1 advancing a position in the virtual queue. In other implementations, the indication can be received when given user 110-1 is at or near the head, i.e., first position, of the virtual queue.

At step 310, the indication of position change can be transmitted from GPI 140-2 to CPHE 105. At step 315, CPHE 105 can generate a queue position notification based on the indication of the change in position. At step 320, the queue position notification can be transmitted to a computing device, such as mobile device 115-1, of given user 110-1 to alert him/her of the change in his/her position in the virtual queue and/or a change in the estimated queue time.

In some implementations, as shown in example method 400 represented in FIG. 4, at step 405 an identity of the prescribed medication(s) can be received at GPI 140-2. This identity can be determined from prescription data 136 corresponding to the medical prescription 135, for example, by a staff member of the given pharmacy reviewing prescription data 136 and determining the identity of the prescribed medication. Alternatively, and/or in addition, additional processing or other automated means can be used to determine the identity of the medication from prescription data 136.

At step 410, the identity of the prescribed medication can be transmitted from GPI 140-2 to CPHE 105 (e.g., as prescription identity data). At step 415, CPHE 105 can retrieve information related to the prescribed medication based on the identity of those medications. CPHE 105 may retrieve this information from a medication information database 150, shown in FIG. 1. CPHE 105 can also access this information over a wired or wireless network from external databases such as government regulatory databases and medical research databases. The information can also be provided by the given pharmacy through GPI 140-2 or by a different pharmacy through its corresponding pharmacy interface, such as GPI-140-1. This information can include, but is not limited to, side-effects of the prescribed medication and interactions of the prescribed mediation with other substances.

At step 420, the information can be communicated from CPHE 105 to given user 110-1. As discussed in relation to step 225 of method 200, the communicating can include, but is not limited to, transmitting the information to mobile device 115-1 of given user 110-1 or to make the information available through a web account of given user 110-1 accessible, for example, through terminal 120-1.

Figure 5:
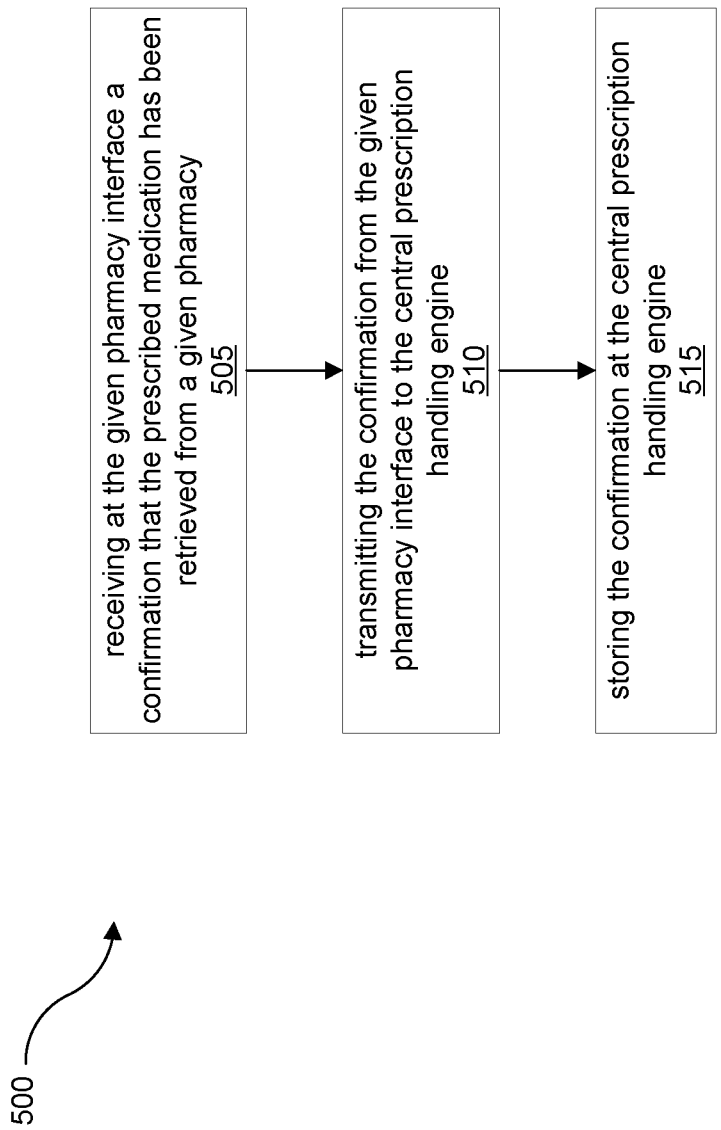
FIG. 5 depicts another example method of filling a medical prescription, according to a non-limiting implementation.

In some implementations, as shown in example method 500 represented in FIG. 5, at step 505 at GPI 140-2 a confirmation can be received that the prescribed mediation has been retrieved from the given pharmacy. This confirmation can be input at GPI 140-2 by a staff member of the given pharmacy, or can be communicated to GPI 140-2 automatically by, for example, IT, sales, or inventory tracking systems of the given pharmacy.

At step 510, the confirmation can be transmitted from GPI 140-2 to CPHE 105. At step 515, the confirmation can be stored at CPHE 105. In some implementations, system 100 can comprise a dedicated database connected to CPHE 105 for storing such confirmations. In some implementations, this dedicated database can be prescription information database 155, shown in FIG. 1. The confirmation information can comprise pharmacy location, staff identifier, retrieval timestamp, medication quantity, and verification method of given user 110-1.

Figure 6:
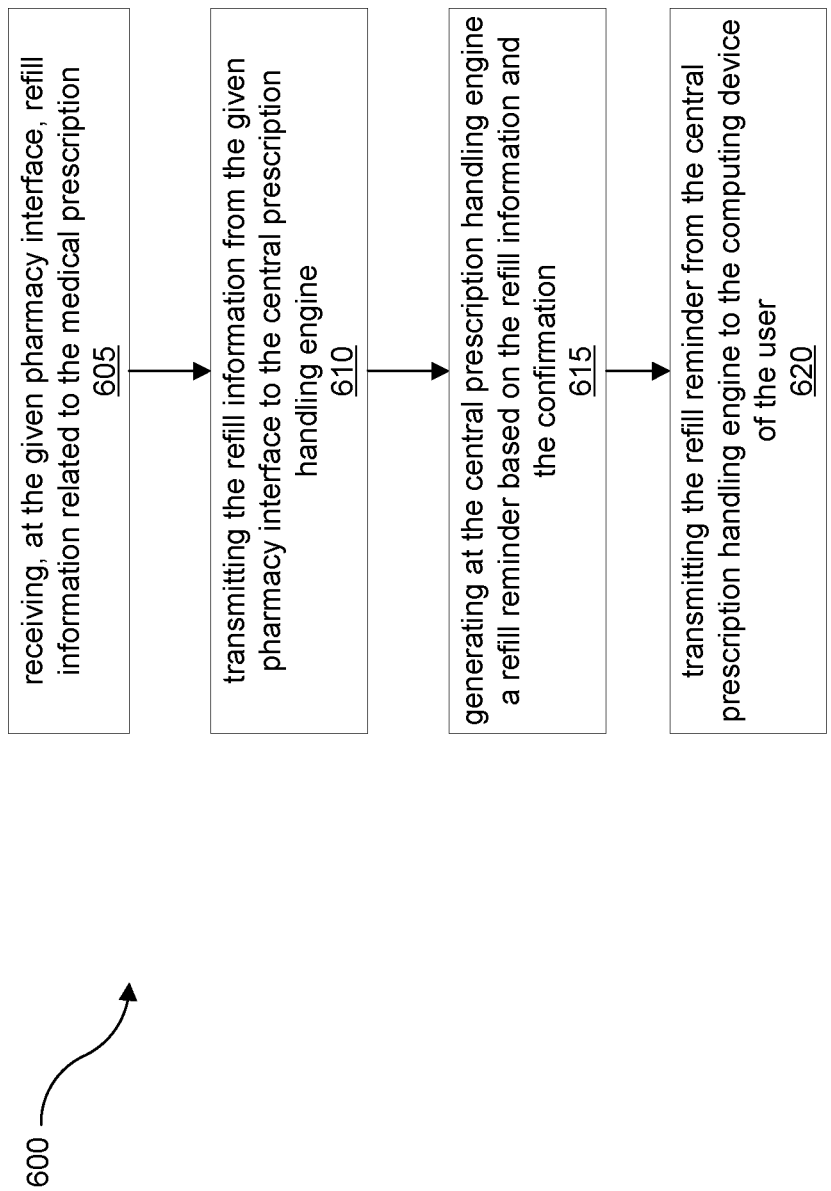
FIG. 6 depicts another example method of filling a medical prescription, according to a non-limiting implementation.

In some implementations, as shown in example method 600 represented in FIG. 6, at step 605 GPI 140-2 can receive refill information related to the medical prescription 135. The refill information can comprise data that is determined from prescription data 136 of medical prescription 135, for example by a staff member at the given pharmacy or by data processing systems and software. Hence, the refill information may also be referred to herein as "refill data". At step 610 the refill information can be transmitted from GPI 140-2 to CPHE 105. At step 615, a refill reminder can be generated at CPHE 105, based on the refill information and the confirmation that the prescribed medication has been retrieved from the given pharmacy. At step 620, the refill reminder can be transmitted from CPHE 105 to a computing device of given user 110-1, such as mobile device 115-1. In other implementations, the refill reminder can instead and/or additionally be communicated to a web account of given user 110-1, which can be accessible, for example, through terminal 120-1.

Figure 7:
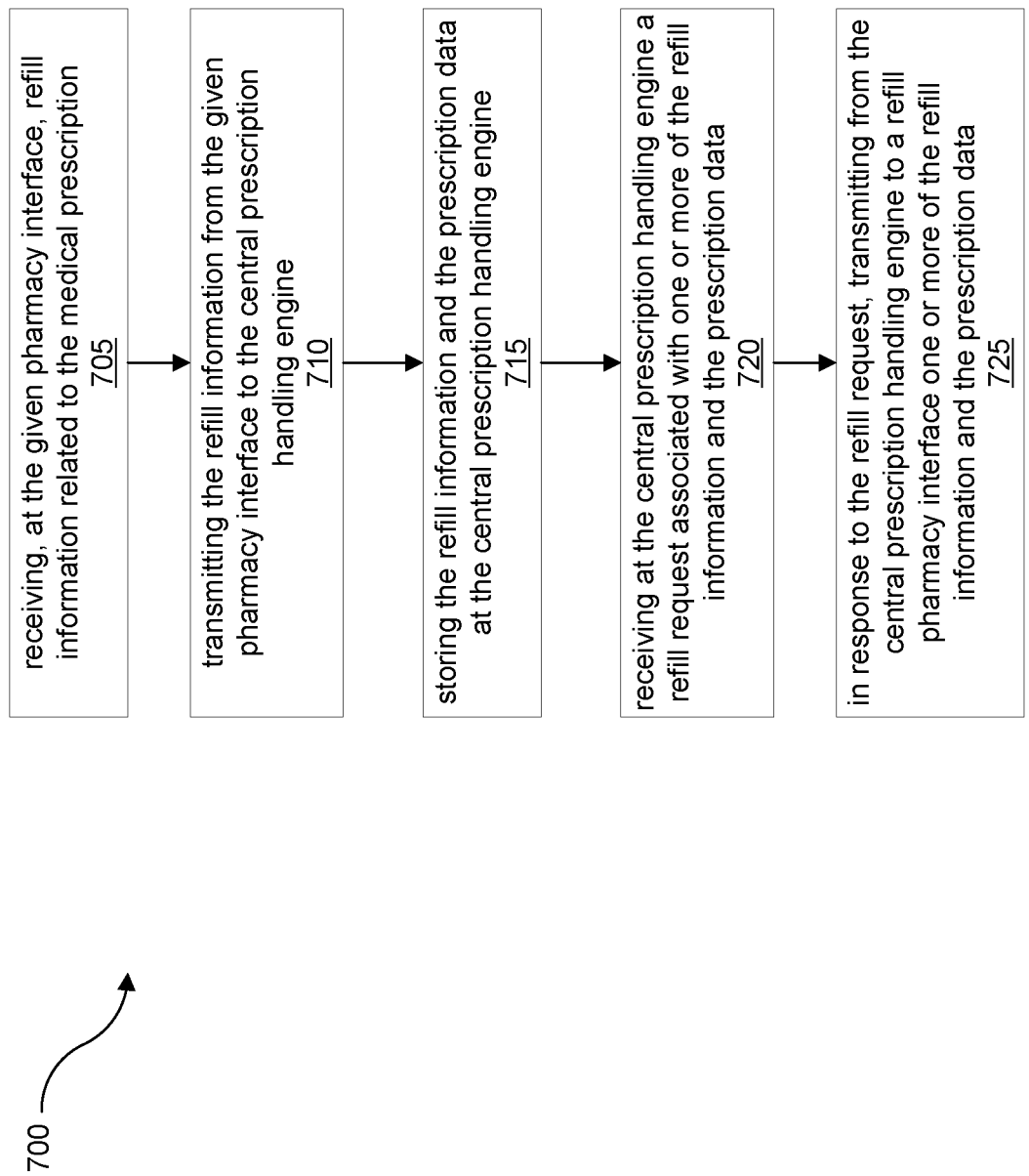
FIG. 7 depicts another example method of filling a medical prescription, according to a non-limiting implementation.

In some implementations, as shown in example method 700 represented in FIG. 7, at step 705 GPI 140-2 can receive refill information related to the medical prescription 135. The refill information can comprise data that is determined from prescription data 136, for example by a staff member at the given pharmacy or by data processing systems and software (e.g., image processing systems and software for the implementations in which the prescribed data 136 comprises image 137), and as such is also referred to herein as refill data. At step 710 the refill information can be transmitted from GPI 140-2 to CPHE 105. At step 715, the refill information and prescription data 136 of medical prescription 135 can be stored at CPHE 105. In some implementations, the refill information and prescription data 136 can be saved in prescription information database 155 in communication with CPHE 105.

At step 720 CPHE 105 can receive a refill request associated with one or more of the refill information and prescription data 136. For example, give user 110-1 may use mobile device 115-1 or terminal 120-1 to submit such a refill request to CPHE 105. This request can reference the refill information and/or prescription data 136 and seek a refill based on medical prescription 135 whose prescription data 136 was previously submitted to CPHE 105. Given user 120-1 may choose not to resubmit to CPHE 105 the prescription data 136 of medical prescription 135 to obtain the refill. At step 725, in response to the refill request, CPHE 105 can transmit to a refill pharmacy interface one or more of the refill information and prescription data 136 of medical prescription 135.

The refill pharmacy interface can be GPI 140-2, or it can be any other one of pharmacy interfaces 140-1-140-n. The choice of refill pharmacy interface can be made by given user 110-1 and submitted to CPHE 105 through mobile device 115-1 or terminal 120-1. In the alternative, and/or additionally, the choice of refill pharmacy can be made automatically by CPHE 105 based on default criteria or based on criteria selected by given user 110-1 and submitted to CPHE 105.

Figure 8:
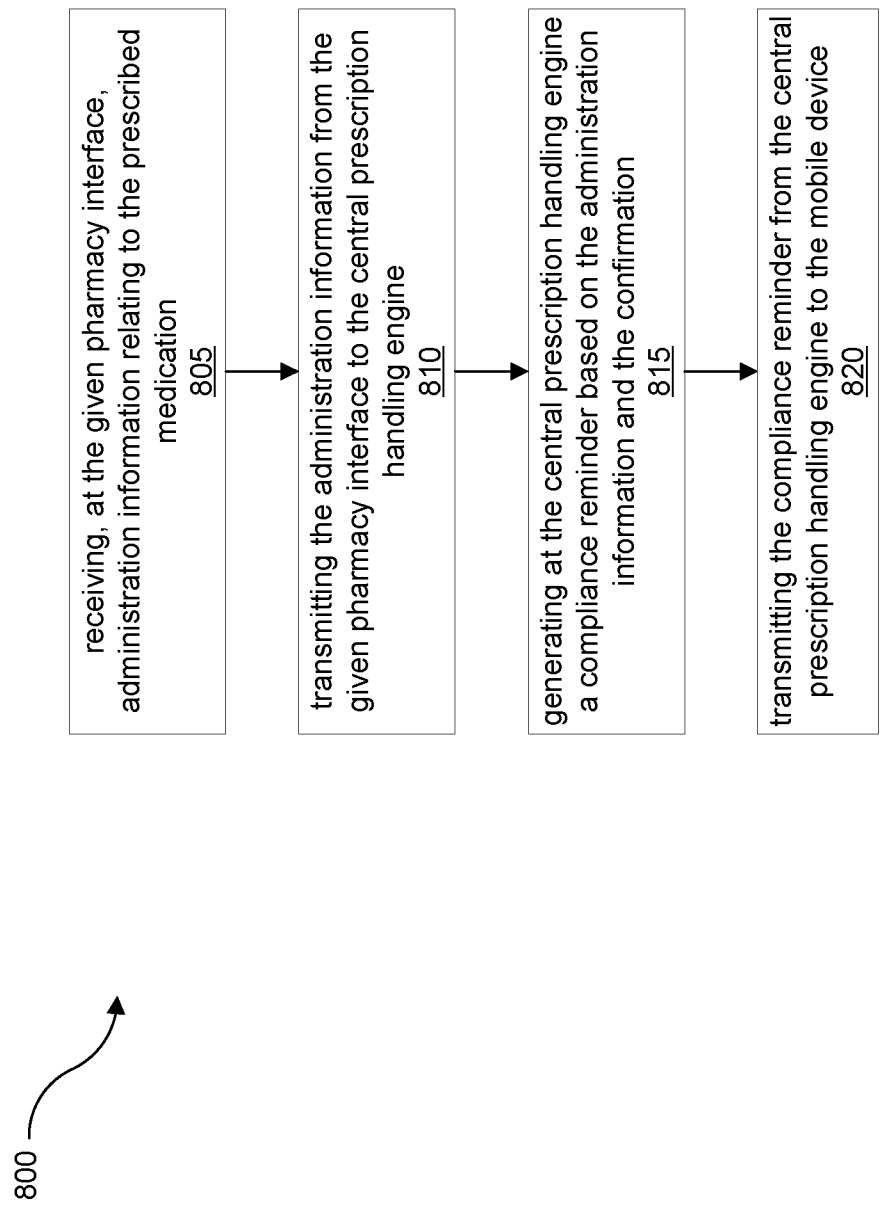
FIG. 8 depicts another example method of filling a medical prescription, according to a non-limiting implementation.

In some implementations, as shown in example method 800 represented in FIG. 8, at step 805 GPI 140-2 can receive administration information related to the prescribed medication. The administration information comprise data that is determined from prescription data 136, for example by a staff member of the given pharmacy or by data processing systems and software, and as such is also referred to herein as administration data. Administration information can include, but is not limited to, dose and frequency of administration, and routes of administration such as oral or topical. At step 810, the administration information can be transmitted from GPI 140-2 to CPHE 105. In some implementations, CPHE 105 can store the administration information in prescription information database 155.

At step 815, CPHE 105 can generate a compliance reminder based on the administration information and the confirmation that the prescribed medication was retrieved from the given pharmacy. The confirmation of retrieval can be used as a trigger for the compliance reminders. At step 820, the compliance reminder(s) can be transmitted from CPHE 105 to mobile device 115-1. The type and frequency of reminders can be set by default or selected by given user 110-1. In some implementations, the compliance reminders can be directly added to the list of tasks or to reminders kept at a corresponding application running on mobile device 115-1. The number and frequency of compliance reminders can be based on the medication administration information, such as frequency of administration and type of medication. Reminder notifications can be received by given user 110-1 through app notification, e-mail, and SMS. The content of the reminder notifications can also be defined by given user 110-1.

In some implementations, CPHE 105 can communicate to given user 110-1 available pharmacy information based on one or more given criteria. The available pharmacy information comprises data indicative of a pharmacy's availability to fill the prescription. The available pharmacy information can be communicated to mobile device 115-1 or made available at a web account or a webpage accessible for example via terminal 120-1 and/or via mobile device 115-1, or other computing device accessible by the user 110-1. The criteria for generating a list of available pharmacies can include, but is not limited to: a physical proximity of a candidate pharmacy associated with one of the plurality of pharmacy interfaces 140, such as 140-1, to given user 110-1; hours of operation of the candidate pharmacy; ability of the candidate pharmacy to receive prescription data 136 from CPHE 105; inventory at the candidate pharmacy of the medication listed in the medical prescription 135; a language spoken by staff of the candidate pharmacy; a preferred pharmacy operator a processing capacity of a computing system of the candidate pharmacy; a workload of computer of the candidate pharmacy; and the prescription filling capacity of the candidate pharmacy. In some implementations, the physical proximity of the candidate pharmacy from the given user may be determined based on the output of a Global Positioning System (GPS) receiver of the computing device of the user (e.g., of the mobile device 115-1) and GPS coordinates of the candidate pharmacy interface. In some implementations, the prescription filling capacity is based on predicted staffing levels of the candidate pharmacy at a particular date and/or time, which may increase or decrease based on anticipated demand of the pharmacy's services. In some implementations, the prescription filling capacity may be based on historical information, such as historical staffing levels. In some implementations, the prescription filling capacity may be determined by an automated workflow management system based on at least one of predicted staffing levels and historical information. In some implementations, the preferred pharmacy operator can be operating under a brand of pharmacies.

In some implementations, CPHE 105 comprises a load balancer 119 and generates the available pharmacy information based on at least the output of the load balancer 119. The load balancer 119 may comprise any suitable combination of hardware components that are configured to perform load balancing algorithms to determine the availability of a respective pharmacy. For example, the load balancer 119 can comprise one or more processors configured to execute load balancing instructions that may originate from a data storage, such as data storage 109 or a computer network. For example, in some implementations, the output of the load balancer 119 can be based on at least one of: a history of transmission of prescription data 136 to a respective pharmacy interface and a tested response time of a respective pharmacy interface. In respect of the history of transmission of prescription data, the load balancer 119 may store a count of the number of transmissions of prescription data 136 to the respective pharmacy interface over a period of time and, based on reaching a threshold number of transmissions of prescription information 136 to the respective pharmacy interface, comprise an indication in the availability data that the respective pharmacy of the respective pharmacy interface is not available to fill the prescription. In respect of testing the response time of the respective pharmacy interface, the CPHE 105 may query the respective pharmacy interface and based on exceeding a threshold response time from the respective pharmacy interface, comprise an indication in the availability data that the respective pharmacy of the respective pharmacy interface is not available to fill the prescription.

In some implementations, the availability data comprises a relative ranking of a candidate pharmacy in respect of at least another candidate pharmacy in which the candidate pharmacy is associated with one of the plurality of pharmacy interfaces and the at least another candidate pharmacy associated with at least another one of the plurality of pharmacy interfaces. In some implementations, the criterion is weighted.

Upon communicating the available pharmacy information to given user 110-1, CPHE 105 can receive a selection of a given pharmacy based on the available pharmacy information. This selection can be provided by given user 110-1, for example through mobile device 115-1 or terminal 120-1.

In some implementations, CPHE 105 receives insurance policy identification information provided by given user 110-1, for example through mobile device 115-1 or terminal 120-1. The insurance policy identification information can refer to the identity of any insurance policies that would cover at least a portion of the cost of filling medical prescription 135 of given user 110-1. The insurance policy identification information can then be transmitted from CPHE 105 to GPI 140-2.

Figure 9:
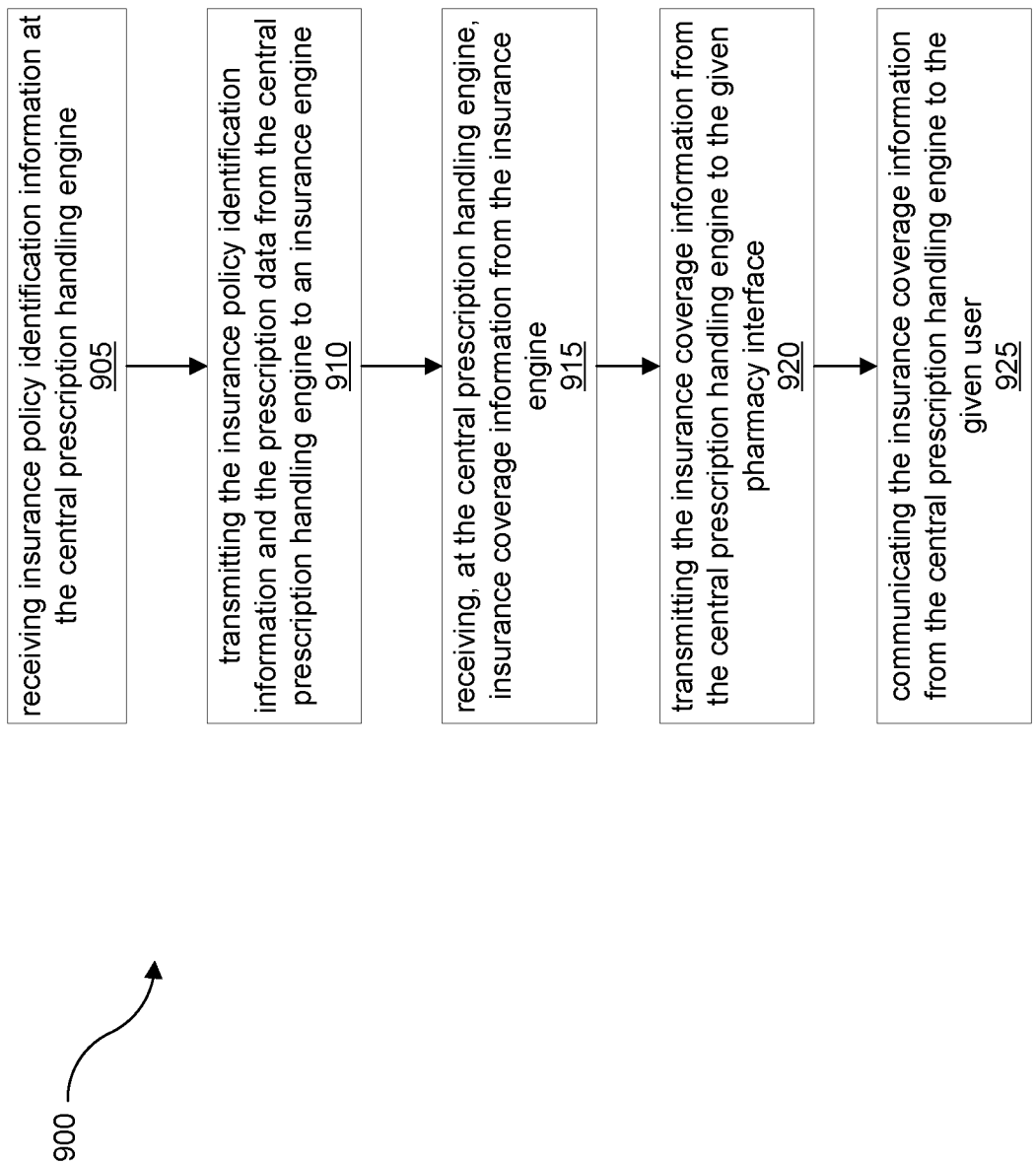
FIG. 9 depicts another example method of filling a medical prescription, according to a non-limiting implementation.

In some implementations, as shown in example method 900 represented in FIG. 9, at step 905 CPHE 105 can receive insurance policy identification information provided by given user 110-1; this information can be provided by given user 110-1, for example through mobile device 115-1 or terminal 120-1. At step 910, CPHE 105 can transmit the insurance policy identification information and image 137 of medical prescription 135 to an insurance engine 160, as shown in FIG. 1. Insurance engine 160 can be in communication with one or more insurance providers. Insurance engine 160 can receive insurance policy identification information from CPHE 105 and retrieve and/or provide insurance coverage details for the identified insurance policy for the prescribed medication and/or coverage plan of given user 110-1. Insurance engine 160 can connect to receive information directly from insurance providers or present information based on insurance policy information provided by given user 110-1.

At step 915, the CPHE 105 can receive insurance coverage information from insurance engine 160, where the insurance coverage information corresponds to the insurance policy identification information. The insurance coverage information also relates to an identity of the prescribed medication determined from prescription data 136 (e.g., image 137 of the medical prescription 135), as described above in relation to step 605. At step 920, CPHE 105 can transmit the insurance coverage information to GPI 140-2. At step 925, CPHE 105 can also transmit the insurance coverage information to given user 110-1, for example by sending the insurance coverage information to mobile device 115-1 and/or making the insurance coverage information available through a web account accessible by terminal 120-1 and/or mobile device 115-1. In this manner, both the given pharmacy and given user 110-1 can be informed of the insurance coverage that given user 110-1 has for the particular medication prescribed.

Figure 10:
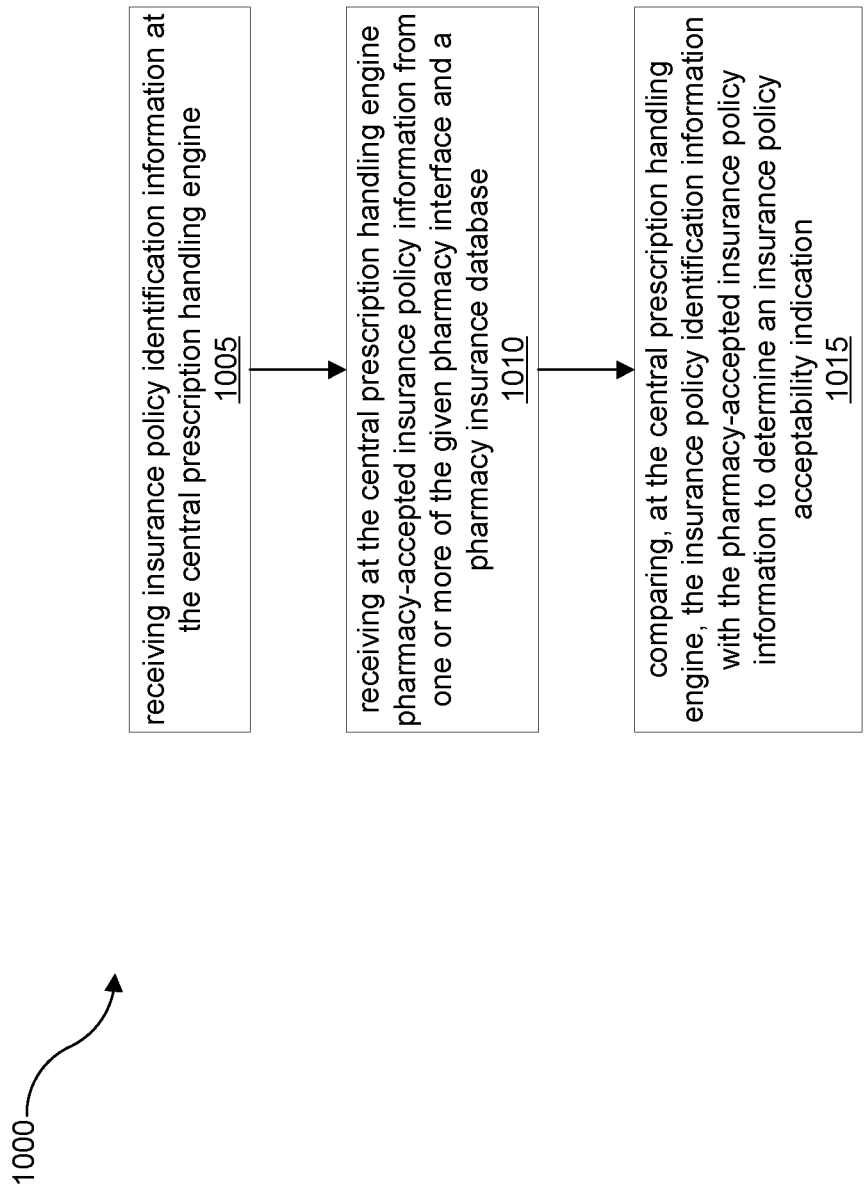
FIG. 10 depicts another example method of filling a medical prescription, according to a non-limiting implementation.

In some implementations, as shown in example method 1000 represented in FIG. 10, at step 1005, CPHE 105 can receive insurance policy identification information provided by given user 110-1, as described above in relation to step 905. At step 1010, CPHE 105 can receive pharmacy-accepted insurance policy information from one or more of GPI 140-2 and a pharmacy insurance database 165 shown in FIG. 1. Pharmacy-accepted insurance policy information can indicate which insurance policies are accepted by the given pharmacy, so that the given pharmacy would apply the coverage at the point of purchase and given user 110-1 would have to pay only for the portion of the cost of the medication not covered by the insurance policy.

Pharmacy-accepted insurance policy information can be provided at GPI 140-2 for example by a staff member of and/or an internal IT system of the given pharmacy. In the alternative, and/or in addition, pharmacy-accepted insurance policy information can be provided by pharmacy insurance database 165, which is in communication with CPHE 105. At step 1015, CPHE 105 can compare the insurance policy identification information with the pharmacy-accepted insurance policy information to determine an insurance policy acceptability indication. This indication can be communicated to given user 110-1 to inform him/her whether the given pharmacy would apply the insurance coverage at the point of purchase, or if the given pharmacy does not accept the insurance policy of given user 110-1. If the insurance policy of given user 110-1 is not accepted by the given pharmacy, then given user 110-1 would have to pay the full price of the medication at the given pharmacy and subsequently submit a claim to his/her insurance provider.

Figure 11:
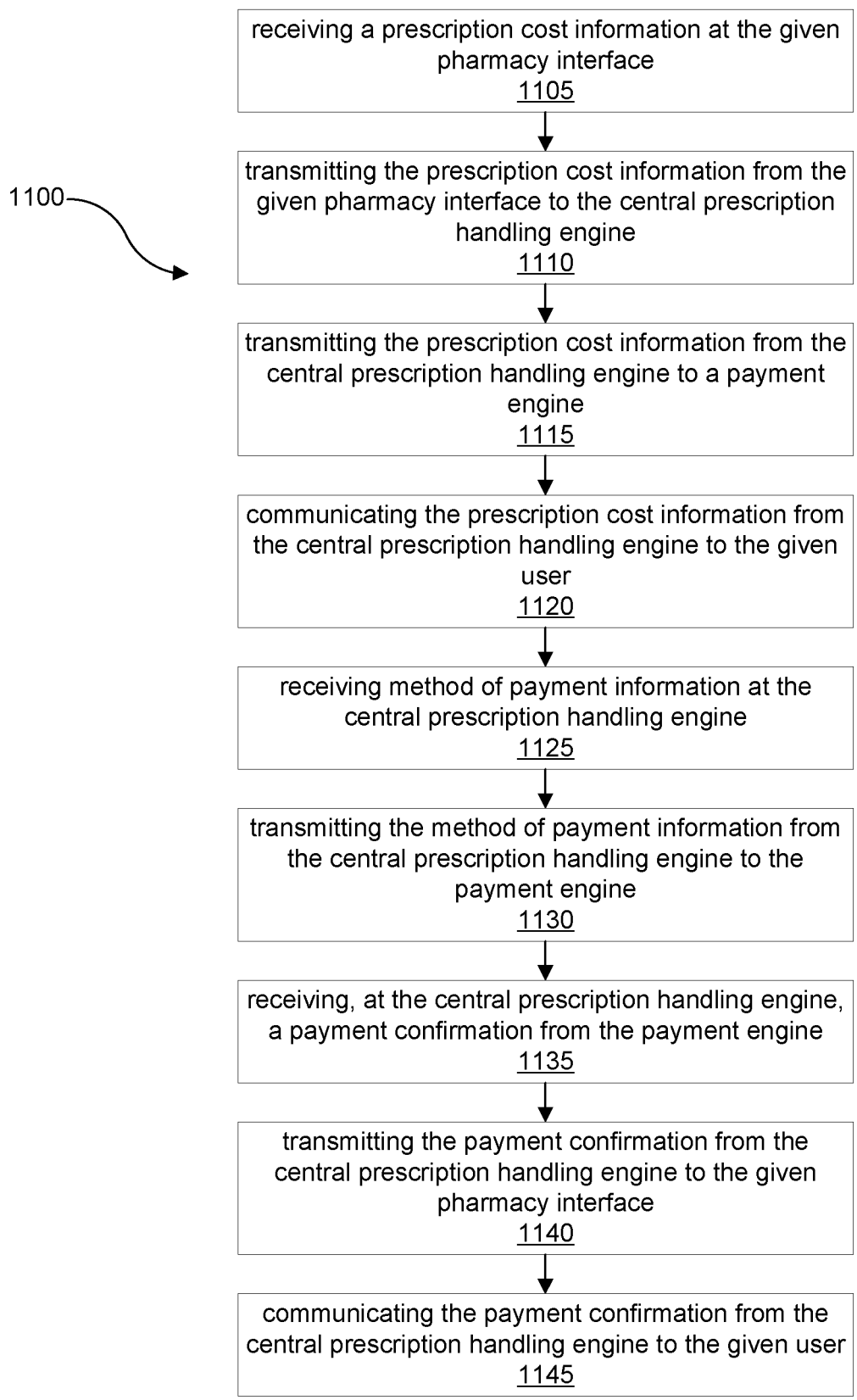
FIG. 11 depicts another example method of filling a medical prescription, according to a non-limiting implementation.

In some implementations, as shown in example method 1100 represented in FIG. 11, at step 1105 GPI 140-2 can receive prescription cost information. Once GPI 140-2 receives prescription data 136 and receives the identity of the medication(s) being sought, the cost information can be provided by a staff member of the given pharmacy and/or by internal inventory, sales, or other IT system of the given pharmacy. At step 1110, GPI 140-2 can transmit the prescription cost information to CPHE 105. At step 1115, the prescription cost information can be transmitted from CPHE 105 to a payment engine 170, shown in FIG. 1. Payment engine 170 can be in communication with a third-party payment processing system, such as a credit card company. Payment engine 170 can receive payment information, such as amount and a credit card number, process the payment itself or by communicating with the third-party payment processing system, and then provide and/or receive a payment confirmation.

At step 1120, CPHE 105 can communicate the prescription cost information to given user 110-1. This communication can comprise sending the cost information to mobile device 115-2 and/or making the cost information available at a web account accessible by terminal 120-1 and/or mobile device 115-1. The prescription cost information can be adjusted to reflect taxes, insurance coverage, and/or shipping and handling costs where applicable.

At step 1125, CPHE 105 can receive method of payment information provided by given user 110-1. The method of payment information can comprise, but is not limited to, credit card information, debit card information, and PayPal™ account information. Given user 110-1 can provide the payment information through mobile device 115-1, for example through a mobile application, or through a web account accessible via terminal 120-1 and/or mobile device 115-1.

At step 1130, CPHE 105 can transmit method of payment information to payment engine 170. The method of payment information can comprise explicitly, or by implication, approval of given user 110-1 to process the payment. At step 1135, CPHE 105 can receive from payment engine 170 a payment confirmation, signifying that the payment was successfully processed. If there are any difficulties with processing the payment, the payment confirmation would instead comprise a message about the nature of those difficulties in processing the payment.

At step 1140, CPHE 105 can transmit the payment confirmation to GPI 140-2, notifying the given pharmacy that the prescription has been paid-for and is ready to be picked up by or shipped to given user 110-1. If there is a difficulty with processing the payment, no payment confirmation would be sent to GPI 140-2, or the payment confirmation would indicate that the payment was not processed successfully and/or indicate the nature of the difficulty. At step 1145, the payment confirmation, indicating either successful payment or difficulty with processing the payment, can be communicated by CPHE 105 to given user 110-1. The communication can comprise transmitting the payment confirmation to mobile device 115-1 and/or making the payment confirmation available at a web account accessible by terminal 120-1 and/or mobile device 115-1.

In some implementations, the scheduling data can comprise an appointment for delivering the prescribed medication to given user 110-1. Such an appointment can comprise a time window during which given user 110-1 can expect to receive the shipped medication.

In some implementations CPHE 105 can receive target delivery date data provided by given user 110-1 through mobile device 115-1 and/or terminal 120-1. CPHE 105 then transmits the target delivery date data to GPI 140-2. If delivery according to the target delivery date data is feasible, then the appointment is scheduled based on the target delivery date data provided by given user 110-1. If, however, delivery according to the target delivery date data is not feasible, the appointment is scheduled based on an alternate target delivery date. A data structure for target delivery date data may comprise a preferred delivery date with one or more time ranges, followed by one or more secondary or alternate delivery dates each with one or more time ranges. The data structure for the target delivery date data may also comprise an indication of an alternate pharmacy of the plurality of pharmacies associated with the plurality of pharmacy interfaces 140 from which the medication that is the subject of the medical prescription 135 will be delivered. For example, in some implementations, the target delivery data may comprise an indication of at least one of: an alternate target delivery date, an alternate target delivery time and alternate pharmacy to the given pharmacy in which the schedule data of that another pharmacy comprises at least one date or time that matches the target delivery date.

In some implementations, the alternate target delivery date can be received at GPI 140-2, or provided by a shipper which can be different from the given pharmacy, as alternate target delivery date data. Feasibility of delivery according to the target delivery date data may also be determined by the given pharmacy and/or the shipper based on factors including, but not limited to, whether the prescribed medication is in stock at the given pharmacy, prescription filling capacity of the given pharmacy, shipping distance, shipping requirements such as specialized packing and customs clearance, and the optimum shipping route. If an alternate delivery date/time is selected by the shipper or the pharmacy, that information is transmitted to given user 110-1 for confirmation. GPI 140-2 will display final delivery date and/or time and/or location confirmed by both pharmacy/shipper staff and given user 110-1.

The system and methods for filling a prescription described above allow each user 110-1 to 110-n to be presented with a list of available pharmacies and provided with the ability to choose which pharmacy will receive the user's prescription image data. CPHE 105 can receive each user's pharmacy selection and routes that user's prescription image data to the pharmacy interface corresponding to the selected given pharmacy. As such, CPHE 105 can reduce the time, bandwidth, and processing power that would be needed if each user had to find and review each available pharmacy individually and potentially communicate with each available pharmacy individually.

Sending prescription data 136 or other data of medical prescription 135 obviates the need for the given user 110-1 and/or medical prescription 135 to be physically present at the selected given pharmacy to initiate the prescription filling process. Once the prescription information is communicated to the given pharmacy, scheduling data related to the filling of medical prescription 135 is communicated from GPI 140-2 to CPHE 105, which in turn routes and communicates the scheduling data to given user 110-1. This allows given user 110-1 to plan around the wait time while medical prescription 135 is being filled.

In addition, CPHE 105 and/or any databases that are in communication with it, can store and track the communications between given user 110-1 and the given pharmacy 140-1 to facilitate provision of continuing and actively-monitored care. For example, CPHE 105 can inform user 110-1 about medication side-effects or interactions, and can remind the user about compliance, i.e. when/how to take the medication, and about prescription refills. Moreover, CPHE 105 can provide a central hub for integrating insurance engine 160 and/or payment engine 170 with the prescription filling process, which can further reduce the time and effort required to complete the prescription filling process. The CPHE can be configured to cross-check previously filled prescriptions to prevent a prescription or copies of a prescription from being filled more than once.

The systems described herein are capable, at least in some implementations, of obtaining information from the user about his/her medical history and experiences with the prescribed medication. For example, the CPHE 105 can transmit a request for experiential information to the given user 110-1 via a computing device of the user, such as mobile device 115-1 and terminal 120-1. The request for experiential information can be transmitted as encrypted data (e.g., as request data 151, FIG. 1) to the computing device and be provided as a survey that is viewable on the mobile device 115-1 or the terminal 120-1. The request for experiential information can request that the user provide answers to questions about ongoing and/or past medication (s), such as experienced side-effects or perceived effectiveness of the medication(s). The response from the user can be transmitted to the CPHE 105 and stored at the CPHE 105 or a data storage unit in communication with the CPHE 105. In some implementations, the response from the user is transmitted to the CPHE 105 as encrypted data, such as experiential response data 153 (FIG. 1).

In some implementations, the systems described herein monitor whether and when a user fills and/or refills a medical prescription and queries the user for follow up information if the medical prescription 135 has not been picked up or delivered to the user within a period of time. For example, in some implementations, the given pharmacy interface 140-2 transmits a prescription delivery notification 171 to the CPHE 105 in response to the medical prescription being delivered and/or picked up (e.g., in response to the user 110-1 picking up the medication or the medication has been delivered to the user). If a period of time passes without the CPHE 105 receiving the prescription delivery notification 171, the CPHE 105 will transmit to a computing device of user 110-1, such as mobile device 115-1 or terminal 120-1, follow up data 172 which comprises a request for follow up information that is viewable at the user's computing device. The follow up data 172 may be provided to the user's computing device in the form of a survey that asks the user questions about why the medical prescription 135 has not been picked up. In some implementations, the period of time is predetermined. In some implementations, the period of time to transmit the follow up data 172 to the user's computing device is based on historical data (such as the average time the user 110-1 has taken to pick up prescriptions over a past amount of time). Similarly, in some implementations, in response to a period of time having passed after the scheduling data 146 has been communicated to the given user 110-1 (via transmission of the scheduling data 146 from the CPHE (such as CPHE 105) to a computing device of the user 110-1) without the CPHE having received availability data from the user 110-1 (via a computing device of the user 110-1) or a refill request (refill request data), the CPHE 105 will transmit the follow up data 172 to the computing device of user 110-1. Again, in some implementations, the period of time is predetermined. In some implementations, the period of time to transmit the follow up data 172 to the user's computing device is based on historical data. For clarity, the period of time to transmit follow up data 172 to a computing device of user 110-1 is also referred to herein as a follow up period of time.

Figure 12:
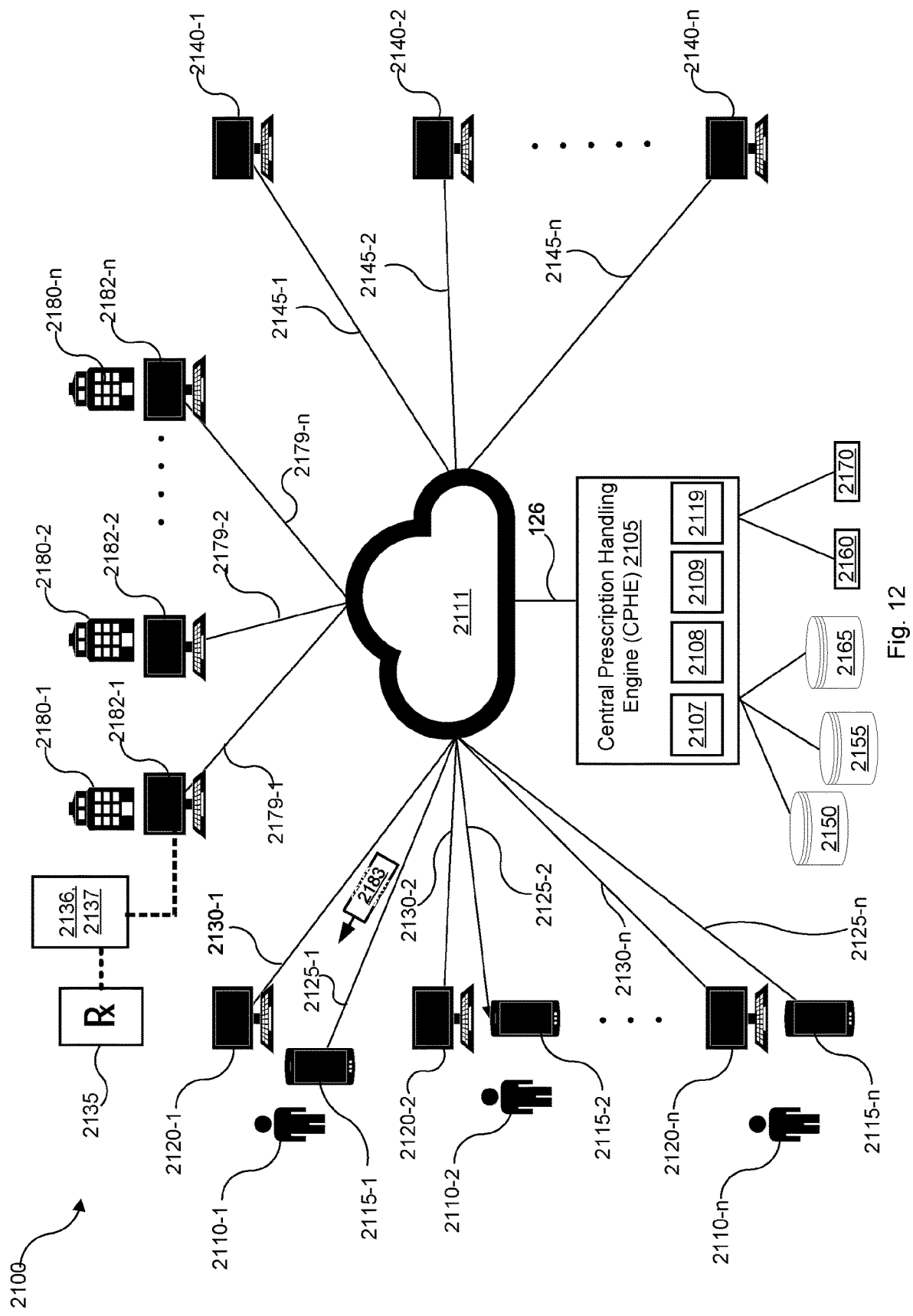
FIG. 12 depicts another example system for filling a medical prescription, according to a non-limiting implementation.

FIG. 12 depicts another implementation of the systems and methods for filling a medical prescription described herein, example system 2100. In the example system 2100, like elements to example system 100 are denoted by like or similar numbers to FIG. 1, however starting with a "21" rather than a "1" (e.g., a mobile device similar to mobile device 115-1 is depicted as mobile device 2115-1). In the example system 2100, the CPHE 2105 is in communication with a plurality of computing devices that are each associated with at least one prescribing entity (referred to individually as prescribing entity 2180-1, 2180-2 to 2180-n, and collectively as prescribing entities 2180), such as a hospital or a clinic. The plurality of computing devices associated with the plurality of prescribing entities 2182 are depicted as prescribing entity computing devices 2182-1, 2182-2 to 2182-n (referred to collectively as prescribing entity computing devices 2182). Each one of the plurality of prescribing entity computing devices 2182 is accessible by a prescriber who is an individual that is authorized by the relevant licensing and/or governmental authority to prescribe medications, such as a physician and a nurse practitioner. The CPHE 2105 is in communication with the plurality of prescribing entity computing devices 2182 via communication links 2179-1, 2179-2 to 2179-n, which may be any combination of wired and/or wireless links suitable for transmitting and receiving data to and from the CPHE 2105.

It is understood that, in some implementations, the prescribing entity computing devices 2182 are representative of prescribing entity interfaces. In such implementations, each one of the prescribing entity interfaces can represent one or more prescribing entities. Furthermore, each of the prescribing entity interfaces can also comprise a connection point between the internal IT systems of the corresponding prescribing entity (or entities) and CPHE 105. The prescribing entity interfaces may, in some implementations, be accessed through a special prescribing entity web account.

In contrast to the example system 100, the prescription data 2136 can also be transmitted from a given prescribing computer of the plurality of prescribing computers 2182, such as prescribing computer 2182-1. Similarly to the example system 100, the prescription data 2136 can comprise an image 2137 of the medical prescription. In some implementations, the image 2134 is captured by the prescribing computing device, such as prescribing computing device 2182-1, or a computing device that is in communication with the prescribing computing device. The prescription data 2136 could be temporarily stored within the prescribing computing device or transmitted from the mobile device to the CPHE 2105 as a compressed and encrypted image file. In some implementations, the prescription data 2136 comprises structured data or metadata (e.g., in Extensible Markup Language (XML), Health Level 7 (HL7) formats) that is associated with the image 2137, but does not comprise the image 2137. In some implementations, the structured data or metadata comprises the image 2137. In other words, in some implementations, the prescription data comprises at least one of the image 2137 and structured data or metadata corresponding to the medical prescription. In some implementations, the structured data or metadata is generated by the prescribing entity computing device, such as prescribing entity computing device 2182-1 without the image 2137. In such implementations, the prescribing data 2136 can be used by the prescribing entity to generate the image 2137 at the respective prescribing entity computer, such as prescribing entity computer 2182-1.

The prescription data 2136 can be transmitted to the CPHE 2105 in various ways. For example, in some implementations, the prescription data 2136 is transmitted to the CPHE 2105 via facsimile, such as a digital eFax, email of the prescription data 2136 and any other suitable mode of transmitting the prescription data 136 described herein. In some implementations, the prescription data 2136 is generated by and transmitted by an electronic medical record (EMR) or electronic health record (EHR) system.

Similarly to the example system 100, the prescription data 2136 can be sent via link 2125-1 to CPHE 2105, which is configured to selectively route the prescription data 2136, for example to pharmacy interface 2140-2, among the plurality of pharmacy interfaces 2140-1 to 2140-n. Selective routing could either be based on user choice, or could be automated using preferences stored by user (pharmacy location/chain, day/time for pick-up/delivery, pharmacy operating hours, insurance coverage, language spoken, medication availability, prescription queue length, pharmacy staff availability, etc). The selective routing can be based on selections of user 2110-1, or can be performed automatically based on characteristics of each pharmacy corresponding to each pharmacy interface 2140-1 to 2140-n, as will be discussed further below.

In response to receiving the prescription data 2136 from the prescribing entity computing device 2182-1, for example, the CPHE 2105 transmits a notification of the medical prescription 2183 to a computing device of a given user associated with the prescription data 2136, such as mobile device 2115-1 or terminal 2120-1 of user 2110-1. The CPHE 2105 processes the received prescription data 2136 to determine an identity of the given user 2110-1. Other than the source of the prescription data 2136 and the transmission of the notification of the medical prescription 2183 of the notification to the computing device of the given user, the example system 2100 can operate similarly to that of example system 100.

Initiating the generation and transmission of the prescription data 2136 from the prescriber (via the prescribing entity), provides a number of advantages. For example, initiating the generation and transmission of prescription data 2136 from the prescriber may, in some implementations, provide some of the following advantages: potentially fewer medication-related errors, potential reduction in the risk of losing paper prescriptions, potential reduction in the risk of privacy breaches (such as the mishandling of paper prescriptions and/or fax transmissions), potentially fewer prescribing errors (improved review and medication reconciliation), potentially better management of patients' chronic conditions or patients using multiple medications (co-ordinating multiple medications, scheduling fills and/or refills), potentially reduced communication between pharmacies, physicians and nurses to clarify information written on prescriptions, potentially fewer dispensing errors, the ability to communicate and engage with a patient if the filled prescription has not been picked up, potentially fewer emergency department visits and hospitalizations because of possible improvements of the medication safety, potential improvement in medication cost management, potentially increased medication compliance and awareness by the pharmacist and physician that the patient has picked up their medication, potential reduction in wait times, potentially increased patient caregiver satisfaction and potentially improved resource management and staffing with load balancing and workflow distribution.

Figure 13:
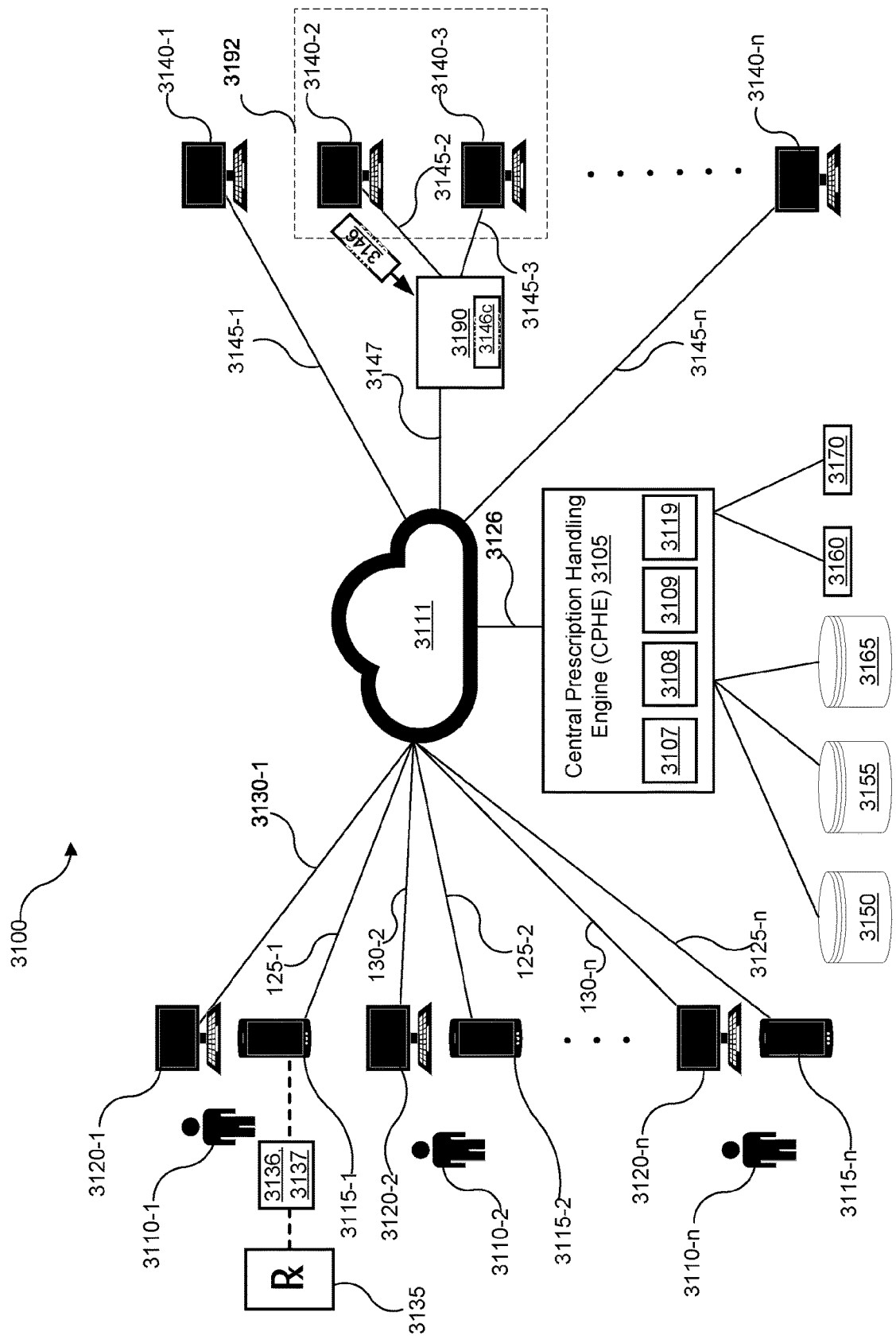
FIG. 13 depicts another example system for filling a medical prescription, according to a non-limiting implementation.

FIG. 13 depicts another example implementation of the systems and methods for filling a medical prescription described herein, example system 3100. In the example system 3100, like elements to example system 100 are denoted by like or similar numbers to FIG. 1, however starting with a "31" rather than a "1" (e.g., a mobile device similar to mobile device 115-1 is depicted as mobile device 3115-1). In the example system 3100, at least two of the pharmacy interfaces 3140, such as pharmacy interface 3140-2 and pharmacy interface 3140-3, are associated with each other. For example, pharmacy interface 3140-2 and pharmacy interface 3140-3 may be owned by the same individual or company, or may be within the same geographical area defined by a municipality, territory, state, province or country.

As depicted in FIG. 13, the example system 3100 comprises an intermediary pharmacy interface 3190 in communication with the CPHE 3105 via communication link 3147 (and link 3126). Communication link 3147 comprises any suitable combination of wired and/or wireless communication links suitable for the transmission and receipt of data by the CPHE 3105. The intermediary pharmacy interface 3190 is in communication with a subset of the plurality of pharmacy interfaces 3192, which comprise, for example, pharmacy interface 3140-2 and pharmacy interface 3140-3. As depicted in FIG. 13, the CPHE 3105 is in communication with the subset of the plurality of pharmacy interfaces 3192 via the intermediary pharmacy interface 3190.

The intermediary pharmacy interface 3190 operates as a centralized processing and computing interface for the subset of the plurality of pharmacy interfaces 3192. For example, in some implementations, at least one of the subset of the plurality of pharmacy interfaces 3192, such as pharmacy interface 3140-2, transmits the scheduling data to the intermediary pharmacy interface 3190. The intermediary pharmacy interface 3190 generates and stores a copy of the received schedule data 3146, as copy of scheduling data 3146c, (e.g., at a database in communication with the intermediary pharmacy interface 3190, not shown) and transmits the received schedule data 3146 to the CPHE 3105 (for communication to the user 3110-1 via at least one computing device of the user 3110-1, such as the mobile computing device 3115-1 or the terminal 3120-1). Instead of transmitting the prescription data 3137 directly to either one of the pharmacy interfaces 3140-2, 3140-3, the CPHE 3105 transmits the prescription data 3137 to the intermediary pharmacy interface 3190. In some implementations, the intermediary pharmacy interface 3190 is virtual pharmacy as described herein with pharmacy capabilities but is not in and of itself a retail pharmacy location. In such implementations, upon receiving the prescription data 3137, the intermediary pharmacy interface 3190 notifies staff at the associated non-retail facility (e.g., by generating an incoming prescription notice that is viewable at a computing device that is associated with the intermediary pharmacy interface 3190). The staff at the associated non-retail facility fill the prescription and the filled prescription is then delivered to the given pharmacy of the subset of the plurality of pharmacy interfaces 3192 from which the user 3110-1 will pick up the filled prescription (e.g., the pharmacy associated with the given pharmacy interface 3140-2). The intermediary pharmacy interface 3190 can then send the prescription data 3137 to the pharmacy interface associated with the pharmacy selected by the user 3110-1 as the pharmacy for picking up the filled prescription. The pharmacy receiving the delivered filled prescription can extract data, via the associated pharmacy interface, from the prescription data 137 to complete the delivery of the filled prescription to the user 3110-1, such as data indicative of the identity of the prescribed medication to confirm that the correct medication and dosage has been provided by the filled prescription. Other data, such as insurance policy identification information, payment information and prescription cost information may also be extracted from the prescription data 137. In some embodiments, this extracted data is sent by the intermediary pharmacy interface 3190 to the pharmacy receiving the filled prescription.

In another example implementation, the user 3110-1 may decide to pick up the filled prescription from the pharmacy associated with the pharmacy interface 3140-2. However, the pharmacy associated with the pharmacy interface 3140-2 may not have sufficient prescription filling capacity to fill the prescribed medication (e.g., the pharmacy may not have the prescribed medication in stock, insufficient staff to fill the prescription, etc.). In such cases, the intermediary pharmacy interface 3190 may determine that the pharmacy associated with the pharmacy interface 3140-3 has sufficient prescription filling capacity based on requested data from each one of the subset of the plurality of pharmacy interfaces 3192 that is indicative of the prescription filling capacity of that respective pharmacy. The intermediary pharmacy interface 3190 may then transmit the prescription data 3137 to pharmacy interface 3140-3 to fill the prescription. After filling the prescription, the pharmacy associated with the pharmacy interface 3140-3 can then deliver the filled prescription to the pharmacy associated with the pharmacy interface 3140-2 for pick up by the user 3110-1 at the appointment time or availability start time indicated by the schedule data 3146. Similarly to the above described implementation, the intermediary pharmacy interface 3190 can then send the prescription data 3137 to the pharmacy interface associated with the pharmacy selected by the user 3110-1 as the pharmacy for picking up the filled prescription, in this case, pharmacy interface 3140-2. The pharmacy receiving the delivered filled prescription can extract data from the prescription data 137, via the associated pharmacy interface, pharmacy interface 3140-2 in this case, to complete the delivery of the filled prescription to the user 3110-1, such as data indicative of the identity of the prescribed medication to confirm that the correct medication and dosage has been provided by the filled prescription. Other data, such as insurance policy identification information, payment information and prescription cost information may also be extracted from the prescription data 137. In some embodiments, this extracted data is sent by the intermediary pharmacy interface 3190 to the pharmacy receiving the filled prescription.

Generally stated, in some implementations where the given pharmacy interface 3140-2 is in communication with the CPHE 3105 via the intermediary pharmacy interface 3190, transmitting the scheduling data 3146 from the given pharmacy interface 3140-2 to the CPHE 3105 (e.g., step 220 depicted in FIG. 2), comprises: transmitting the scheduling data 316 from the given pharmacy interface 3140-2 to the intermediary pharmacy interface 3190 and transmitting the scheduling data 3146 to the CPHE 3105). Further, transmitting the prescription data 3136 from the CPHE 3105 to the given pharmacy interface 3140-2 (e.g., step 210 depicted in FIG. 2) comprises: transmitting the prescription data 3146 from the CPHE 3105 to the intermediary pharmacy interface 3190 instead of the given pharmacy interface 3140-2.

Those skilled in the art will appreciate that in some implementations, the functionality of the CPHE, and the other described system components, can be implemented using pre-programmed hardware or firmware elements (e.g., application specific integrated circuits (ASICs), electrically erasable programmable read-only memories (EEPROMs), etc.), or other related components. In other implementations, the functionality of the CPHE can be achieved using a computing apparatus that has access to a code memory (not shown) which stores computer-readable program code for operation of the computing apparatus. The computer-readable program code could be stored on a computer readable storage medium which is fixed, tangible and readable directly by these components, (e.g., removable diskette, CD-ROM, ROM, fixed disk, USB drive). Furthermore, it is appreciated that the computer-readable program can be stored as a computer program product comprising a computer usable medium. Further, a persistent storage device can comprise the computer readable program code. It is yet further appreciated that the computer-readable program code and/or computer usable medium can comprise a non-transitory computer-readable program code and/or non-transitory computer usable medium. Alternatively, the computer-readable program code could be stored remotely but transmittable to these components via a modem or other interface device connected to a network (including, without limitation, the Internet) over a transmission medium. The transmission medium can be either a non-mobile medium (e.g., optical and/or digital and/or analog communications lines) or a mobile medium (e.g., microwave, infrared, free-space optical or other transmission schemes) or a combination thereof.

The above-described implementations of the invention are intended to be examples of the present invention and alterations and modifications may be effected thereto, by those of skill in the art. The scope of the claims should not be limited by the exemplified embodiments described above, but should be given the broadest interpretation consistent with the description as a whole.

The invention claimed is:

1. A method of filling a medical prescription, comprising:
   receiving at a central prescription handling engine prescription data corresponding to the medical prescription listing a prescribed medication, the central prescription handling engine configured to selectively route the prescription data received at the central prescription handling engine to a given pharmacy interface among a plurality of pharmacy interfaces and to selectively route scheduling data received at the given pharmacy interface for being communicated to a computing device;
   transmitting the prescription data from the central prescription handling engine to the given pharmacy interface;
   receiving at the given pharmacy interface the scheduling data corresponding to the prescription data;
   transmitting the scheduling data from the given pharmacy interface to the central prescription handling engine;
   communicating the scheduling data from the central prescription handling engine to the computing device;
   communicating, from the central prescription handling engine to the computing device, available pharmacy information data based on a given criterion, wherein the central prescription handling engine is in communication with a load balancer configured to perform load balancing algorithms and the available pharmacy information data is based on at least an output of the load balancer; and receiving at the central prescription handling engine a selection of a given pharmacy based on the available pharmacy information data, the selection provided via the computing device.

2. The method of claim 1, wherein the given pharmacy interface is in communication with the central prescription handling engine via an intermediary pharmacy interface, and wherein:

transmitting the scheduling data from the given pharmacy interface to the central prescription handling engine comprises transmitting the scheduling data from the given pharmacy interface to the intermediary pharmacy interface, and transmitting the scheduling data from the intermediary pharmacy interface to the central prescription handling engine; and transmitting the prescription data from the central prescription handling engine to the given pharmacy interface comprises transmitting the prescription data from the central prescription handling engine to the intermediary pharmacy interface instead of the given pharmacy interface.

3. The method of claim 2, wherein the intermediary pharmacy interface is associated with a subset of pharmacy interfaces of the plurality pharmacy interfaces that comprises the given pharmacy interface.

4. The method of claim 1, wherein the prescription data comprises at least one of an image of the medical prescription and structured metadata of the medical prescription.

5. The method of claim 2, wherein the receiving at the central prescription handling engine the prescription data corresponding to the medical prescription listing the prescribed medication comprises receiving the prescription data from one of the computing device and a computing device of a prescribing entity.

6. The method of claim 5, wherein the prescription data comprises an image that is captured at one of the computing device and generated by the computing device of the prescribing entity.

7. The method of claim 5, wherein at least a portion of the prescription data is generated by the computing device of the prescribing entity.

8. The method of claim 1, wherein the method further comprises:

in response to receiving the prescription data, transmitting a notification of the medical prescription to the computing device from the central prescription handling engine.

9. The method of claim 1, wherein the communicating comprises transmitting the scheduling data over a network from the central prescription handling engine to the computing device.

10. The method of claim 1, wherein the communicating comprises making available the scheduling data through at least one of a web account and a web portal accessible by a given user via the computing device.

11. The method of claim 1, wherein the scheduling data comprises at least one of an appointment for attending at the given pharmacy to retrieve the prescribed medication and an indication of a start time from which the prescribed medication is available for retrieval from the given pharmacy.

12. The method of claim 11, wherein the appointment and the indication of the start time are determined based on at least one of an availability of the prescribed medication at the given pharmacy and a prescription filling capacity of the given pharmacy.

13. The method of claim 11, further comprising:

receiving user availability data at the central prescription handling engine from the computing device; and transmitting the user availability data from the central prescription handling engine to the given pharmacy interface;

wherein the appointment and the indication are scheduled based on the user availability data.

14. The method of claim 1, wherein the scheduling data comprises a position of a given user in a virtual queue at the given pharmacy.

15. The method of claim 14, further comprising:

receiving at the given pharmacy interface an indication that the position of the given user in the virtual queue has changed;

transmitting the indication from the given pharmacy interface to the central prescription handling engine;

generating, at the central prescription handling engine, a queue position notification based on the indication; and transmitting the queue position notification from the central prescription handling engine to the computing device to alert the given user of the change in the position of the given user in the virtual queue.

16. The method of claim 1, further comprising:

receiving at the given pharmacy interface an identity of the prescribed medication, the identity of the prescribed medication determined from the prescription data of the medical prescription;

transmitting, from the one of the given pharmacy interface and another pharmacy interface of the plurality of pharmacy interfaces, the identity to the central prescription handling engine;

retrieving, at the central prescription handling engine, information data related to the prescribed medication based on the identity; and communicating the information data related to the prescribed medication from the central prescription handling engine to the computing device.

17. The method of claim 1, further comprising:

receiving, at the given pharmacy interface, refill information data related to the medical prescription, the refill information data determined from the prescription data of the medical prescription;

transmitting the refill information data from the given pharmacy interface to the central prescription handling engine;

storing the refill information data and the prescription data of the medical prescription at the central prescription handling engine;

receiving at the central prescription handling engine a refill request associated with one or more of the refill information data and the prescription data of the medical prescription; and in response to the refill request, transmitting from the central prescription handling engine to a refill pharmacy interface one or more of the refill information data and the prescription of the medical prescription.

18. The method of claim 1, further comprising:

receiving at the given pharmacy interface confirmation data that the prescribed medication has been retrieved from the given pharmacy;

transmitting the confirmation data from the given pharmacy interface to the central prescription handling engine;
storing the confirmation data at the central prescription handling engine;
receiving, at the given pharmacy interface, administration information data relating to the prescribed medication, the administration information data determined from the prescription data of the medical prescription;
transmitting the administration information data from the given pharmacy interface to the central prescription handling engine;
generating at the central prescription handling engine a compliance reminder based on the administration information data and the confirmation data; and
transmitting the compliance reminder from the central prescription handling engine to the computing device.

19. The method of claim 1, wherein the given criterion comprises one or more of:
a physical proximity of a candidate pharmacy to a given user, the candidate pharmacy being associated with at least one of the plurality of pharmacy interfaces;
hours of operation of the candidate pharmacy;
ability of the candidate pharmacy to receive the prescription data from the central prescription handling engine;
processing capacity of a computing system of the candidate pharmacy and a workload of the computing system of the candidate pharmacy;
inventory at the candidate pharmacy of the medication listed in the medical prescription;
the language spoken by staff of the candidate pharmacy;
a preferred pharmacy operator; and
a prescription filling capacity of the candidate pharmacy.

20. The method of claim 1, further comprising:
receiving insurance policy identification information data at the central prescription handling engine, the insurance policy identification information data received from the computing device; and
transmitting the insurance policy identification information data from the central prescription handling engine to the given pharmacy interface.

21. The method of claim 1, further comprising:
receiving a prescription cost information data at the given pharmacy interface;
transmitting the prescription cost information data from the given pharmacy interface to the central prescription handling engine;
transmitting the prescription cost information data from the central prescription handling engine to a payment engine;
communicating the prescription cost information data from the central prescription handling engine to the computing device;
receiving method of payment information data at the central prescription handling engine, the method of payment information data via the computing device;
transmitting the method of payment information data from the central prescription handling engine to the payment engine;
receiving, at the central prescription handling engine, payment confirmation data from the payment engine; and
transmitting the payment confirmation data from the central prescription handling engine to the given pharmacy interface; and
communicating the payment confirmation data from the central prescription handling engine to the computing device.

22. The method of claim 1, wherein the scheduling data comprises an appointment for delivering the prescribed medication to a given user.

23. The method of claim 13, further comprising:
when a follow-up period of time has passed after the communicating of the scheduling data from the central prescription handling engine to the computing device without receiving the user availability data at the central prescription handling engine,
transmitting follow-up data to the computing device, the follow-up data comprising a request for follow up information data that is viewable at the computing device.

* * * * *